United States Patent
Tsunetomo et al.

(10) Patent No.: US 6,919,961 B2
(45) Date of Patent: Jul. 19, 2005

(54) ADHERING SUBSTANCE DETECTOR AND CONTROLLER USING THE SAME

(75) Inventors: Keiji Tsunetomo, Osaka (JP); Fumitoshi Kobayashi, Osaka (JP); Hideki Imanishi, Osaka (JP); Harunobu Yoshida, Osaka (JP); Masahide Wakisaka, Osaka (JP); Tatsumi Tokuda, Osaka (JP)

(73) Assignee: Niles Co., Ltd., Tokyo (JP)

( * ) Notice: Subject to any disclaimer, the term of this patent is extended or adjusted under 35 U.S.C. 154(b) by 177 days.

(21) Appl. No.: 10/276,131

(22) PCT Filed: May 10, 2001

(86) PCT No.: PCT/JP01/03918

§ 371 (c)(1),
(2), (4) Date: Nov. 12, 2002

(87) PCT Pub. No.: WO01/86259

PCT Pub. Date: Nov. 15, 2001

(65) Prior Publication Data

US 2003/0156291 A1 Aug. 21, 2003

(30) Foreign Application Priority Data

May 12, 2000 (JP) .................................. 2000-140761

(51) Int. Cl.[7] .............................................. G01N 21/55
(52) U.S. Cl. .................... 356/445; 356/448; 250/208.1; 250/227.25; 250/574
(58) Field of Search .................... 356/445, 446, 356/447, 448; 340/602; 318/483; 250/227.24, 227.25, 208.1, 574

(56) References Cited

U.S. PATENT DOCUMENTS

| | | | | |
|---|---|---|---|---|
| 4,701,613 A | * | 10/1987 | Watanabe et al. | ........... 340/602 |
| 4,867,561 A | | 9/1989 | Fuji et al. | |
| 5,572,315 A | * | 11/1996 | Krell | ........... 356/136 |
| 5,661,303 A | * | 8/1997 | Teder | ....... 250/227.25 |
| 5,898,183 A | * | 4/1999 | Teder | ........... 340/602 |
| 5,991,049 A | * | 11/1999 | Tanaka et al. | ........... 356/445 |
| 5,998,782 A | * | 12/1999 | Koyama et al. | ....... 250/227.25 |

(Continued)

FOREIGN PATENT DOCUMENTS

| | | |
|---|---|---|
| JP | 57-134657 | 2/1981 |
| JP | 59-152449 | 10/1984 |
| JP | 63-33645 | 2/1988 |
| JP | 63-038058 | 2/1988 |
| JP | 64-25036 | 12/1989 |

*Primary Examiner*—Michael P. Stafira
*Assistant Examiner*—Juan D. Valentin, II
(74) *Attorney, Agent, or Firm*—Hamre, Shumann, Mueller & Larson, P.C.

(57) ABSTRACT

An object sensor is provided, which has a high object detection rate with respect to an object such as a raindrop adhering to a detection surface, and which is capable of detecting the presence/absence of an object with a high sensitivity. A light source 10, a detection surface 110, a focusing lens 40, and a plurality of photodetecting elements of a photodetecting unit 50 form a focusing system of equal magnification that is capable of catching an image in a size smaller than an object to be detected. Light emitted from the light source 10 is incident on the detection surface 110 via a prism 20 at a predetermined incident angle. Without a raindrop 120, the total internal reflection condition is satisfied as shown by a path 140 of a beam, so that the beam is subjected to the total internal reflection. Then, the beam passes through a prism 30, and is focused on a photodetecting surface of the photodetecting unit 50 by the focusing lens 40. On the other hand, with a raindrop 120, the total internal reflection condition is not satisfied as shown by a trail 130 of a beam, so that the beam passes therethrough and is not focused on the photodetecting unit 50. A difference in signal level is determined on the photodetecting element basis, so that an object covering the detection surface 110 is detected.

17 Claims, 17 Drawing Sheets

U.S. PATENT DOCUMENTS 6,064,059 A * 5/2000 Pientka et al. ............... 318/483
6,207,967 B1 * 3/2001 Hochstein .............. 250/227.25
6,232,603 B1 * 5/2001 Nelson ................... 250/227.25
6,262,407 B1 * 7/2001 Teder ......................... 318/483
6,307,198 B1 * 10/2001 Asakura et al. .............. 340/602
6,369,378 B1 * 4/2002 Lamm et al. ............... 318/483
6,376,824 B1 * 4/2002 Michenfelder et al. ..................... 250/227.25

* cited by examiner

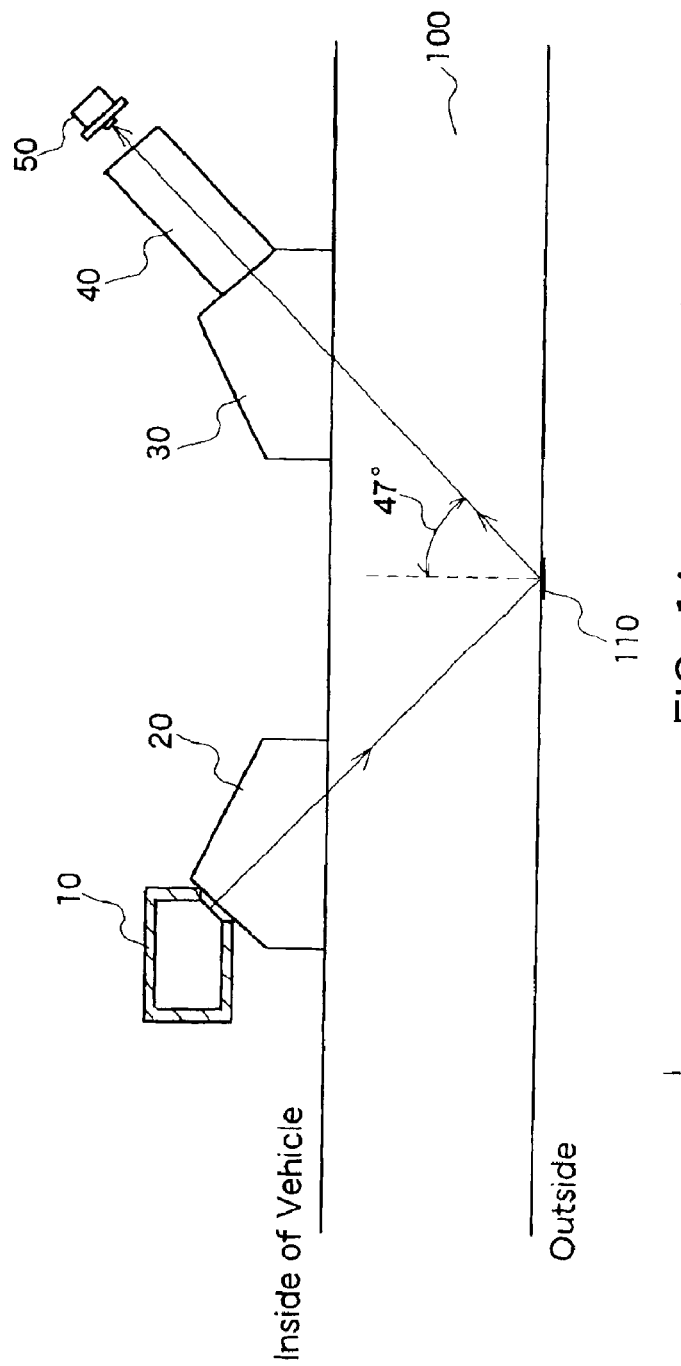
FIG. 1A
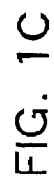
FIG. 1C
FIG. 1B

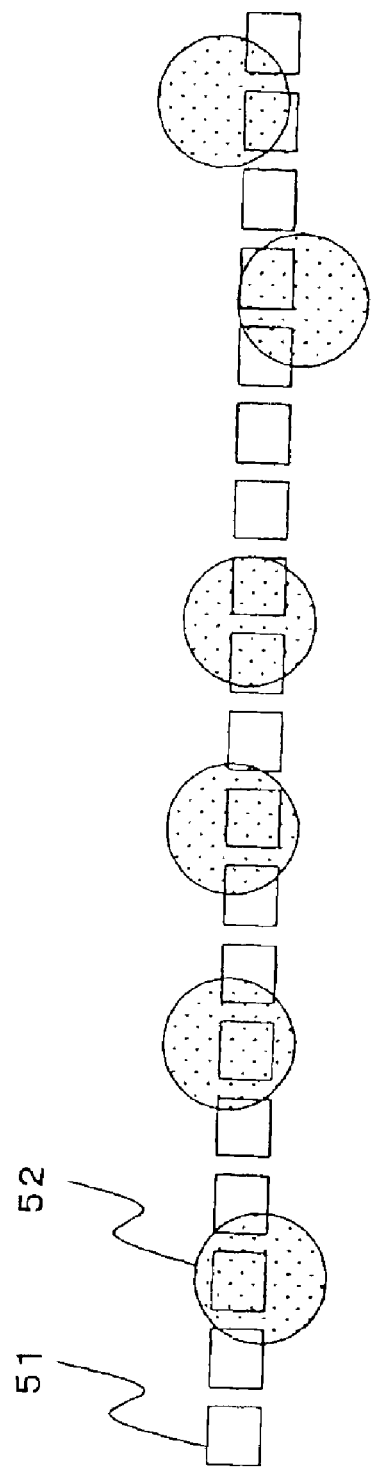

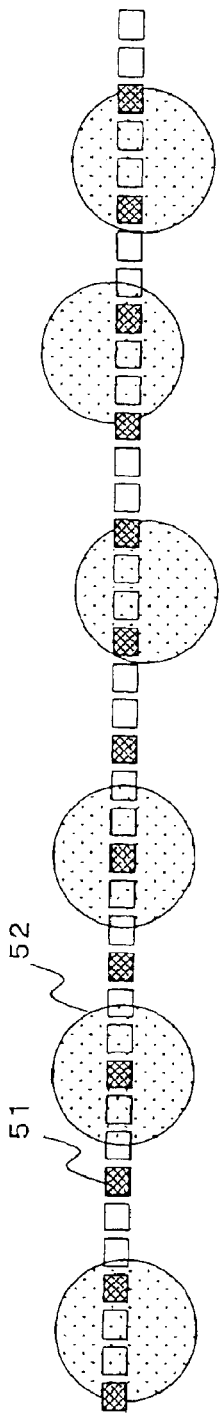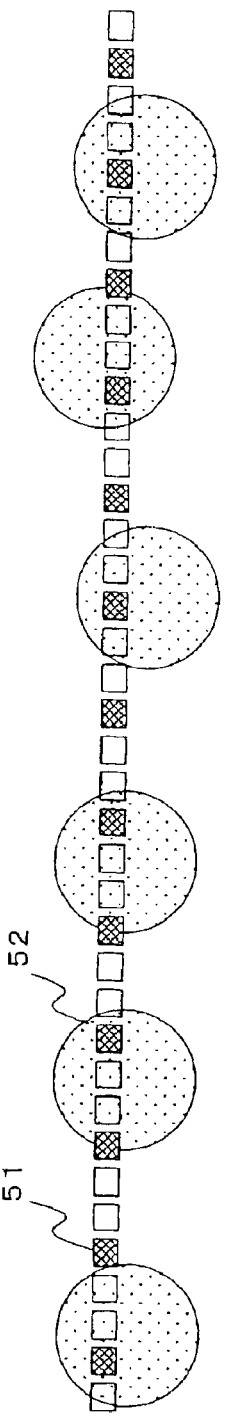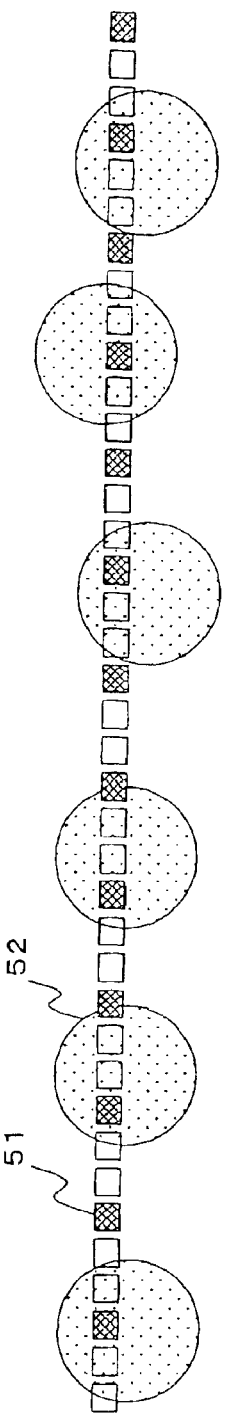

ADHERING SUBSTANCE DETECTOR AND CONTROLLER USING THE SAME

TECHNICAL FIELD

The present invention relates generally to an object sensor for detecting the presence of an object that adheres to a detection surface, and a controller employing the object sensor, which makes a change in control status in response to the detection of the presence of an object by the object sensor.

BACKGROUND ART

There are various systems that detect the presence/absence of an object, and make a change in control status in response to the detection of the presence of an object. Assuming raindrops as an example of such an object, a windshield wiper controller for a windshield of a vehicle needs to make a change in control status thereof as circumstances demand, in response to the start of rain as a change in the weather. One of the important tasks to improve the convenience of the window wiper controller is the development of a rain sensor for detecting whether it is raining. The following will describe, as a conventional object sensor, a conventional rain sensor for detecting raindrops on a windshield of a vehicle as objects adhering thereto.

In the case of a manually-controlled window wiper that is used widely, a driver him/herself has to recognize the start of raining, consider a driving state of the vehicle and a change in an amount of raindrops adhering to a windshield, and manually turn on a window wiper switch that has been turned off, so as to secure the vision through the windshield that is indispensable while the driver drives the vehicle. To reduce the inconvenience of the manual switching operation of the window wiper, a rain sensor is provided to detect the presence of an object such as raindrops on a detection surface of the windshield of the vehicle, and determine whether the wiping of the window is necessary.

Among conventional rain sensors, a reflected-light-detecting-type rain sensor is known, which is classified as such by the raindrop detecting method. FIG. 17 is a view for simply explaining the raindrop detecting principle of a conventional reflected-light-detecting-type rain sensor. In FIG. 17, 1000 denotes a windshield of a vehicle. For conveniences in description, a space above the windshield 1000 indicates the inside of a vehicle, that is, the space on the driver side, and a space below the windshield 1000 indicates the outside of the vehicle. 1010 denotes a light source. 1020 denotes a prism for guiding light of the light source into the inside of the windshield. 1030 is a prism for guiding reflected light out of the inside of the windshield. 1040 denotes a lens. 1050 denotes a photodetecting element, and 1110 denotes a detection surface. 1120 denotes a raindrop adhering to the detection surface. Luminous flux that flares out to cover the entire detection surface is emitted from the light source 1010, and 1130 denotes a path of, among the foregoing luminous flux, a beam having been incident on a portion of the detection surface where a raindrop adheres, while 1140 denotes a path of a beam other than the beam 1130, which has been incident on a portion of the detection surface to which no raindrop adheres.

In the reflected-light-detecting-type rain sensor, it is important to select the angles (mounting angles) at which elements are mounted and properties of the materials (refractive indices of materials in particular) of the same. To describe the raindrop detecting principle briefly, light having been incident on the raindrop-adhesion portion in the detection surface leaks out to the outside since the total internal reflection condition is not satisfied on an external surface of the windshield 1000 on the outside of the vehicle, whereas light having been incident on a portion of the detection surface to which no raindrop adheres is subjected to the total internal reflection since the total internal reflection condition is satisfied on the external surface of the windshield 1000. Then, a difference between intensities of the reflected lights is determined.

Therefore, for the light source 1010 and the prism 1020, angles and materials thereof are selected so as to satisfy a condition of incidence for causing the emitted light to enter the inside of the windshield 1000, as well as the angles further being set so that the light is subjected to the total internal reflection at the detection surface in the external surface of the windshield 1000. Furthermore, an incident angle of light to the detection surface is selected so that the switching between the satisfaction and the failure of the total internal reflection condition on the detection surface 1110 can be caused according to a change in the refractive index caused by adhesion of raindrops.

For the prism 1030, an angle and a material thereof are selected so as to satisfy a condition for causing reflected light to exit the windshield 1000 to the outside, that is, so as not to satisfy the total internal reflection condition. Angles of the lens 1040 and the photodetecting element 1050 and a distance therebetween are selected so that light entering the lens 1040 is focused on a sensor portion of the photodetecting element 1050.

It should be noted that these elements 1010 to 1050 are mountable at locations other than the windshield 1000, for instance, on the hood or on the roof. However, a state to be detected is a state of the windshield 1000, and it is therefore preferable that the elements are mounted on a portion of the windshield 1000. Further, they preferably are mounted so as not to limit the driver's vision. For example, they preferably are mounted at a windshield portion behind a rear-view mirror, where the vision is already restricted because of the rear-view mirror.

To describe an operation of the foregoing conventional reflected-light-detecting-type rain sensor briefly, the luminous flux emitted from the light source 1010 is guided to the inside of the windshield 1000 by the prism 1020, so as to be incident over the entirety of the detection surface 1110. Here, it is assumed that a raindrop 1120 adheres to the detection surface 1110. Among the light incident on the detection surface 1110, the beam 1130 incident on the raindrop 1120-adhesion portion leaks out to the outside of the vehicle since the total internal reflection condition is not satisfied since the raindrop whose refractive index n is approximately 1.3 is present on the external surface of the windshield 1000. Therefore, the leaking beam is not incident on the photodetecting element 1050, and hence, it is not detected. On the other hand, among the light incident on the detection surface 1110, the beam 1140 incident on the portion without raindrops thereon is subjected to the total internal reflection since the total internal reflection condition is satisfied because of the presence of air whose refractive index n is 1 on the external surface of the windshield 1000. Then, on an internal surface of the windshield 1000 on the inside of the vehicle, the beam having been subjected to the total internal reflection is not subjected to the total internal reflection because of the presence of the prism 1030 thereon, thereby exiting toward the inside of the vehicle. The exiting beam is focused on the photosensor portion of the photodetecting element 1050 by the lens 1040.

Thus, an amount of light detected by the photodetecting element 1050 decreases because of the presence of the raindrops 1120, and the amount of the detected light decreases as an area of the detection surface 1110 covered with the raindrops 1120 increases. The change in the amount of light is detected, to detect the presence of raindrops on the detection surface 1110. This is the raindrop detecting principle of the conventional reflected-light-detecting-type rain sensor.

It should be noted that the rain sensor of the aforementioned type is configured so as to output a raindrop detection signal when it detects a change in a signal as described above. The raindrop detection signal from the rain sensor is fed to a control section of the window wiper, and in response to the input of the raindrop detection signal, a predetermined window wiper control and the like is carried out.

However, the conventional rain sensor has the following problems.

As mentioned regarding the prior art, since a raindrop detection reliability depends on a detection area, the detection surface 1110 is provided so as to have as large an area as possible to improve the raindrop detection reliability, and reflected light from the detection surface 1110 is received by a single photodetecting element 1050, so as to detect a change in the reflected light amount. For instance, from the necessity of ensuring the driver's vision through the windshield 1000 and for the purpose of not impairing the appearance of the vehicle, the rain sensor is disposed at a portion of the windshield in the vicinity of the rear-view mirror, etc., and as large an area as possible is obtained there for the detection surface use.

However, the reflected-light-detecting-type rain sensor of the prior art has a problem in its sensitivity. The conventional reflected-light-detecting-type rain sensor is required to detect a change in an amount of reflected light from the detection surface 1110 of the windshield 1000 with a high sensitivity, but the following problems make it difficult to catch a change in the reflected light amount caused by the raindrop adhesion to the windshield 1000 with a high sensitivity.

Generally, a situation in which the driver recognizes the presence of an object such as raindrops on the windshield and feels it necessary to wipe the windshield with a wiper is a situation in which raindrops in a size recognizable by the driver each adhere to the windshield. In other words, the adhesion of raindrops in the foregoing size has to be detected also on the detection surface on the windshield. In the case where a detection surface is prepared on the windshield at a position in a range that can be wiped by window wipers and in the vicinity of the rear-vision mirror, it is assumed that the presence of an object with an area ratio at a level of 0.5% to 1% has to be detected, though depending on the driver's ability of recognition. Here, taking characteristics of a photodetection signal of the reflected-light-detecting-type rain sensor of the prior art into consideration, since a light signal is detected by focusing the reflected light from the entirety of the detection surface on the photodetecting element by the lens, the reflected light amount from the entire detection surface determines a reference signal value, and only the light that exits the windshield through the raindrop-adhesion portion in the detection surface to the outside of the vehicle is involved in determining the change in the signal. Consequently, in the photodetection signal attributed to the entire detection surface, a decrease in the photodetection signal that is attributed to the raindrop-adhesion portion, for instance, a decrease of 0.5% in the photodetection signal, has to be detected. Considering that the operation is carried out in a hostile environment on the windshield of a driving vehicle with noise caused by incidence of external light and the like, normally it is extremely difficult to detect a small signal change of, for instance, 0.5%. Therefore, in the prior art, depending on a difference between an area of the detection surface 1110 and an area occupied by a raindrop to be detected, a change in the entire detection signal is likely to be buried therein.

For the above-described reason, with the conventional reflected-light-detecting-type rain sensor, it is difficult to detect a change caused by adhering raindrops in the reflected light amount with a high sensitivity.

Furthermore, regarding the conventional reflected-light-detecting-type rain sensor, there are several matters to be studied with a view to the high-sensitivity detection of a change in the reflected light amount caused by the adhesion of raindrops.

The first matter to be studied is the removal of influences of external light. The windshield 1000 is composed of a transparent substrate made of glass or the like. External light from the outside of the vehicle, including natural light such as sunlight, artificial illumination such as streetlight, neon signs, etc., and headlights of oncoming vehicles, tends to be incident on the windshield 1000, the prism 1030, the lens 1040, and the photodetecting element 1050, and is likely to be received as light noises. An amount of light that is reflected from the detection surface 1110 and focused by the lens 1040 determines a reference signal value, and a change in the signal is determined by only an amount of light that exits to the outside of the vehicle through the raindrop-adhesion portion in the detection surface 1110. In the case where an amount of the external light is significant relative to the amount of the change in the signal, it is difficult to determine whether there is a change in the detected signal fed from the photodetecting element. This leads to a problem of deterioration of the sensitivity in detecting the adhesion of raindrops.

The second matter to be studied is the selection of an angle at which light from the light source 1010 is incident on the detection surface 1110 and a refractive index of the transparent substrate so that the switching between the satisfaction and the failure of the total internal reflection condition on the detection surface 1110 can be made according to the presence/absence of an object adhering thereto. Here, an angle at which the light emitted from the light source 1010 is incident on the detection surface 1110, a property (refractive index) of the material of the windshield 1000, and a property (refractive index) of the object are to be studied mainly.

The third matter to be studied is the arrangement of elements with an angular aperture of the lens 1040 and mounting angles of the elements taken into consideration. The lens 1040 is used for receiving from the prism 1030 the light reflected by the detection surface 1110, and focusing the same on the photodetecting element 1050. The lens 1040 has an angular aperture, and this also influences the likeliness of catching external light. The angular aperture of the lens 1040 and the mounting angle of the elements have to be selected so that the lens 1040 does not catch the external light, and catches only the reflected light from the detection surface 1110. Here, a reflection angle of the reflected light from the detection surface 1110, an angle at which the light exits the windshield 1000, a property (refractive index) of a material of the prism 1030, an angular aperture of the lens 1040, a mounting angle of the lens, etc. are to be studied.

The fourth matter to be studied is the reduction of light loss in a transparent substrate such as the windshield 1000. Even a transparent substrate exhibits light loss at a ratio according to the properties of a material thereof when light is transmitted therethrough. In the case where the light loss is significant, this causes a problem of a decrease in the amount of reflected light to be received by the photodetecting element 1050.

DISCLOSURE OF THE INVENTION

In light of the foregoing problems, it is an object of the present invention to provide an object sensor that is capable of sensing objects such as raindrops at a high detection rate and determining the presence/absence of objects such as raindrops with a high sensitivity, and a controller employing the foregoing object sensor.

Furthermore, in light of the foregoing problems, it is an object of the present invention to provide an object sensor in which, with influences of external light being eliminated, the satisfaction/failure of the total internal reflection condition on the detection surface is switched therebetween with a high sensitivity according to the presence/absence of an object thereon and the loss of light to be detected is small, so that the presence/absence of objects such as raindrops can be determined with a high sensitivity, as well as to provide a controller employing the object sensor.

To achieve the foregoing objects, an object sensor of the present invention is configured as follows. Light emitted from a light-emitting unit and entering a transparent substrate is reflected on a portion of a surface of the transparent substrate as a detection surface. The light-emitting unit, the transparent substrate, and a photodetecting unit are arranged so that the light reflected from the detection surface is received by the photodetecting unit. An object sensing unit is provided for sensing the presence of an object on the detection surface by detecting a change in a photodetection signal obtained as a result of photodetection of the photodetecting unit, the change being caused by a change in a reflection condition on the detection surface that is caused by the object. The photodetecting unit includes a plurality of micro-photodetecting elements.

With the foregoing configuration, the presence/absence of an object on a portion of the detection surface provides a significant influence on changes in photodetection signals of the micro-photodetecting elements corresponding to the portion of the detection surface, and this makes it possible to binarize the change as a digital signal. Furthermore, respective photodetection signals detected by the micro-photodetecting elements may be arranged according to the arrangement of the micro-photodetecting elements so that a signal pattern (waveform) is obtained. A difference in the reflection condition appears as a digital value or a relative variance in micro-domains in the signal pattern. In the present invention, there is no need to analyze absolute values of signal levels, and it is possible to detect the presence/absence of adhering raindrops by analyzing digital values and changes in a waveform of the signal pattern.

Next, in the object sensor of the present invention, the photodetecting surface of the photodetecting unit and the detection surface form a focusing optical system.

The foregoing configuration allows each micro-photodetecting element of the photodetecting unit to receive the light reflected from the corresponding portion of the photodetection surface in a focused state. Therefore, it is possible to check variances in the reflection condition on the detection surface in detail. Therefore, it is possible to determine the presence/absence of a small object with a high sensitivity, and to check a whole detection surface, thereby ensuring a high object detection rate.

Furthermore, with the object sensor of the present invention thus configured, the detection performance does not deteriorate even if the detection surface is expanded.

It should be noted that an object sensor of the present invention has a focusing optical system, whose measurement principle allows the object sensor to basically to have a great S/N ratio and a high sensitivity. Therefore, even if light from the detection surface is not focused accurately on the photodetecting surface, the characteristic of the present invention is not impaired as long as the great S/N ratio is secured, and such a configuration falls in the technological scope of the present invention.

Furthermore, a configuration even with defocus associated with the size of raindrops or mounting errors falls in the technological scope of the present invention likewise.

Next, in the object sensor of the present invention, each micro-photodetecting element preferably has a size smaller than a size of an image of an object to be sensed that is formed on the photodetecting unit.

The foregoing configuration makes it possible to detect the presence of the object on the detection surface. Further, since the size of each micro-photodetecting element is smaller than that of the image of the object to be sensed, the image being formed on the photodetecting unit, the presence/absence of an object on a portion of the detection surface provides a significant change in a photodetection signal of a micro-photodetecting element corresponding to the portion. Therefore, it is possible to determine the presence/absence of the object with a high sensitivity. Furthermore, since a change in the photodetection signal is extremely significant as described above, the high sensitivity can be maintained even with fluctuations of the photodetection signals caused by characteristic changes of a light-emitting element. Furthermore, since an object is detected by a plurality of micro-photodetecting elements, an area of the detection surface to be detected by the plurality of micro-photodetecting elements is secured, whereby the object detection rate can be maintained.

Here, each micro-photodetecting element preferably has an effective area of not greater than $0.2 \text{ mm}^2$, more preferably, not greater than $0.03 \text{ mm}^2$.

With the foregoing configuration concerning the effective area of each micro-photodetecting element, in the case where the detection surface is a surface of a vehicle windshield and the object is a raindrop, the object with the size of a raindrop that is assumed to be on the windshield can be determined with a high sensitivity. For instance, in the case of a raindrop with a diameter of 0.5 mm, an effective area of not more than $0.2 \text{ mm}^2$ will suffice for the detection with a high sensitivity. In the case of a raindrop with a diameter of 0.2 mm, an effective area of not more than $0.03 \text{ mm}^2$ will suffice for the detection with a high sensitivity.

Next, in the object sensor of the present invention, the plurality of micro-photodetecting elements of the photodetecting unit preferably are arranged in a linear form, or in a two-dimensional form.

With the foregoing configuration, in the case where the plurality of micro-photodetecting elements are arranged in a certain linear form such as a straight line, a curving line, or a broken line, the presence/absence of an object on the line is detected. In the case where the plurality of micro-photodetecting elements are arranged in a two-dimensional form, such as a matrix form, a polygonal form, or a circular form, the presence/absence of an object in the two-dimensional form can be detected.

Next, in the object sensor of the present invention, it is preferable that the object sensor is configured so that a shape of the object on the detection surface can be presumed based on the arrangement of the plurality of micro-photodetecting elements and variances in a signal pattern obtained from the photodetection signals of the arranged micro-photodetecting elements.

With the foregoing configuration, by analyzing variances in the signal pattern, it is possible to identify, among the arranged micro-photodetecting elements, micro-photodetecting elements in which the photodetection signals have varied, whereby it is possible to presume an approximate size and shape of an object referring to the arrangement of the micro-photodetecting elements.

Here, the focusing optical system preferably is a focusing system of equal magnification. A focusing system of equal magnification enables the micro-photodetecting element to receive the reflected light from the detection surface at equal magnification, and provides correct correspondence therebetween.

Here, it is preferable that the focusing optical system is a focusing system of equal magnification formed with a rod-lens array, for example, or a focusing system of equal magnification formed with a graded refractive index lens array.

The foregoing configuration makes it possible to provide an optical focusing lens of equal magnification in an array configuration or the like at low cost, and it can be used as a focusing optical system interposed between the detection surface and the micro-photodetecting elements.

It should be noted that the foregoing object sensor may be configured so that each micro-photodetecting element preferably has a size smaller than a size of an image of the object formed on the photodetecting unit, and so that the photodetecting surface of the photodetecting unit and the detection surface form a focusing optical system.

In the foregoing configuration, since the size of each micro-photodetecting element is smaller than that of the image of the object to be sensed, the image being formed on the photodetecting unit, and each micro-photodetecting element receives the reflected light from the corresponding portion of the detection surface in a focused state, a significant change occurs in a photodetection signal of the micro-photodetecting element corresponding to the portion due to the presence/absence of an object on the corresponding portion of the detection surface. Furthermore, it is possible to check changes in the reflection condition on the detection surface in detail, whereby the presence/absence of the object can be determined with a high sensitivity. Therefore, it is possible to determine the presence/absence of a small object, and to check the entirety of the detection surface. This ensures an object detection rate.

Furthermore, the following will describe a pitch at which the micro-photodetecting elements are arranged. The following describes an example in which the optical system is a focusing system of equal magnification and the photodetecting unit is composed of micro-photodetecting elements arranged in a linear form.

In the case where an area of the micro-photodetecting element is smaller than a size of an image formed on the photodetecting unit of the object to be sensed, the detection sensitivity is determined according to the pitch at which the micro-photodetecting elements are arranged. For instance, assuming that the object to be detected is a raindrop, in the case where the arrangement pitch of the micro-photodetecting elements is set to be not more than approximately ½ of a diameter of the raindrop, it is possible to detect raindrops with a high sensitivity.

More specifically, let the arrangement pitch of the micro-photodetecting elements 51 be p, let the length of each micro-photodetecting element 51 in the arrangement direction (direction indicated by an arrow in FIG. 14) be A, and let a diameter of an object to be sensed be D, as shown in FIG. 14. In this case, the relationship of $D \geq p+A$ should be satisfied. This relationship applies to the case where all the micro-photodetecting elements operate. The relationship in the case where a group composed of micro-photodetecting elements at every n positions (n is a natural number) in the arrangement of the micro-photodetecting elements are caused to operate will be described later.

In the case where the relationship is set as described above, a probability that an entire portion of the detection surface corresponding to one micro-photodetecting element is covered with a raindrop rises significantly. Therefore, the micro-photodetecting elements corresponding to the covered portion have an output of approximately 0. As a result, the S/N ratio of an output of the photodetecting element array rises significantly, thereby improving the detection sensitivity. Thus, an output with a high S/N ratio as described above makes it possible to determine whether a raindrop adheres or not. This simplifies the circuitry and control, thereby providing a low-cost rain sensor.

Furthermore, in the case where each micro-photodetecting element has a size smaller than a size of an image of an object to be sensed that is formed on the photodetecting unit, or more specifically, it has a size of not more than approximately ⅓ the size of the image, a sufficiently high sensitivity can be maintained even if all the arranged micro-photodetecting elements are not used in the detection.

For example, among image sensors available in the market, those with rough sensitivities have arrangement pitches of in the order of 200 dpi (8 dot/mm). In such cases, micro-photodetecting elements are arranged at a pitch of approximately 125 $\mu$m, and a photodetecting window size is approximately 100 $\mu$m. A view schematically illustrating the relationship between the arrangement of the micro-photodetecting elements 51 and images 52 of raindrops that are formed on the photodetecting unit is shown in FIG. 15. If the photodetecting window size is of such an order, it can be considered that the size is sufficiently small relative to the minimum size of raindrops to be detected (diameter: approximately 0.2 mm). Among image sensors available in the market, those of 600 dpi (24 dot/mm) are becoming more readily available. Such an image sensor has an arrangement pitch of the micro-photodetecting elements 51 of 42 $\mu$m, and a length of each micro-photodetecting element of approximately 40 $\mu$m. Therefore, it can be considered that the micro-photodetecting element 51 is sufficiently small relative to each image 52 of raindrops in the minimum size (diameter: approximately 0.2 mm) to be detected, which is formed on the photodetecting unit. In this case, for instance, a group composed of micro-photodetecting elements at every three positions may be driven as shown in FIGS. 16A to 16C in sampling data. Even in this case, a sufficiently high sensitivity can be maintained. It should be noted that in FIGS. 16A to 16C, hatched squares indicate micro-photodetecting elements that are operating, and non-hatched squares indicate micro-photodetecting elements that are not operating. This sampling operation makes it possible to reduce the controlling operation.

Here, in the case where the micro-photodetecting elements are driven at every n positions (n: natural number), assuming that the arrangement pitch of the micro-photodetecting elements is p, the arrangement pitch of the micro-photodetecting elements that are actually operating is n·p. The length A of the micro-photodetecting elements in the arrangement direction and the diameter D of the object to be detected may satisfy the relationship expressed as D≧n·p+A. Under such a relationship, the micro-photodetecting elements may be dealt with in a state of being divided into groups, each group being composed of the micro-photodetecting elements at every n positions, that is, as a residue system of n. In the case where n is set to be 3, the micro-photodetecting elements are divided into three groups. FIGS. 16A to 16C schematically illustrate the three groups.

By operating the micro-photodetecting elements at every n positions, even if a certain micro-photodetecting element does not work because of aging or the like, the group of the micro-photodetecting elements to operate may be changed to another group appropriately, so that an object can be detected without impairing the detection sensitivity.

Furthermore, in the case where a raindrop to be detected occupies a part of a portion of the detection surface corresponding to one certain micro-photodetecting element, and a signal value detected in such a state is in the vicinity of a threshold value with which the presence/absence of an object is determined, the object in such a state can be detected also with high precision, by changing the group of micro-photodetecting elements to be driven to another group appropriately so as to obtain a signal value.

Furthermore, it is possible to carry out the detection operation by changing the number n appropriately according to the size of the detection object. For instance, in the case where the object to be detected is large raindrops, the detection speed is more important than the detection sensitivity. In this case, if the value n may be increased in the detection operation, the number of data to be sampled decreases, thereby increasing the detection speed of the control circuit. On the other hand, in the case where the object to be detected is fine raindrops, the detection sensitivity is more important than the detection speed. In this case, the value n may be decreased in the detection operation, whereby the detection sensitivity can be improved. It should be noted that all the micro-photodetecting elements may be used in the detection operation, without limiting the number of the micro-photodetecting elements to n.

Next, in the object sensor of the present invention, it is preferable that arrangement angles of the light-emitting unit, the transparent substrate, the focusing optical system, and the photodetecting unit are selected according to a refractive index of a material present between outside and the photodetecting unit so as to prevent external light that enters the transparent substrate from directly entering the photodetecting unit.

The foregoing configuration makes it possible to block external light so that the external light does not enter the photodetecting unit directly, thereby ensuring a decrease in light noise stemming from external light. This makes it possible to improve the detection of the presence/absence of an object.

It should be noted that in the foregoing object sensor, the arrangement angles of the light-emitting unit, the transparent substrate, the focusing optical system, and the photodetecting unit preferably are selected so as to satisfy the following formula (1):

$$\sin^{-1}\left(\frac{n_1}{n_3}\right) + \left(\frac{\theta_S}{n_3}\right) < \theta_S \quad (1)$$

where $n_1$ represents a refractive index of a medium on an outside surface side of the transparent substrate, $n_3$ represents a refractive index of a medium present between the transparent substrate and the focusing optical system, $\theta_S$ represents a mounting angle of the focusing optical system, and $\theta_S$ represents an angular aperture of the focusing optical system.

Next, in the foregoing object sensor, the light-emitting unit, the transparent substrate, the focusing optical system, and the photodetecting unit preferably are arranged so that light emitted from the light-emitting unit and reflected on the detection surface enters the photodetecting unit in the case where the object is absent on the detection surface. Besides, the arrangement angles of the light-emitting unit, the transparent substrate, the focusing optical system, and the photodetecting unit preferably are selected so that, in the case where the object is present on the detection surface, a change in the reflection condition on the detection surface caused by the object causes light emitted from the light-emitting unit not to be reflected on the detection surface.

With the foregoing configuration, the satisfaction/failure of the total internal reflection condition on the detection surface is switched with a high sensitivity according to the presence/absence of an object. Therefore, the presence/absence of an object can be determined with a high sensitivity.

It should be noted that in the foregoing object sensor, the arrangement angles of the light-emitting unit, the transparent substrate, the focusing optical system, and the photodetecting unit preferably are selected so as to satisfy the following formula (2):

$$\sin^{-1}\left(\frac{n_1}{n_3}\right) < \theta_2 < \sin^{-1}\left(\frac{n_1'}{n_3}\right) \quad (2)$$

where $n_1$ represents a refractive index of a medium on an outside surface side of the transparent substrate, $n_3$ represents a refractive index of a medium present between the transparent substrate and the focusing optical system, $n_1'$ represents a refractive index of the object, and $\theta_2$ represents an angle of refraction at which the light is refracted upon entry to the transparent substrate.

It should be noted that the object sensor preferably is configured so as to satisfy the foregoing formulae (1) and (2).

Next, in the object sensor of the present invention, in the selection of the arrangement angles of the light-emitting unit, the transparent substrate, the focusing optical system, and the photodetecting unit, the arrangement angles are selected so that a path inside the transparent substrate along which the light emitted by the light-emitting unit and reflected on the detection surface travels is minimized in length.

The foregoing configuration reduces light loss in the transparent substrate such as a windshield, and makes it possible to maintain the relative variances in the photodetection signal according to the presence/absence of photodetection by the photodetecting unit.

The object sensor of the present invention can be configured so that the object to be sensed is a raindrop and the detection surface is provided on a windshield of a vehicle so that the object sensor is used as a rain sensor for detecting presence of a raindrop adhering to the windshield.

Furthermore, to solve the foregoing problems, a controller employing the object sensor of the present invention includes the object sensor used as the rain sensor, a window wiper driving unit, and a window wiper controlling unit. The window wiper controlling unit receives a detection signal concerning an object from the object sensor, and changes control status of the window wiper driving unit according to the detection signal.

The foregoing configuration makes it possible to provide a window wiper device that is capable of detecting the presence of an object such as a raindrop on the detection surface, surely and immediately executing the determination of whether or not the cleaning of the window is necessary, and starting the window wiper driving at an appropriate timing.

BRIEF DESCRIPTION OF DRAWINGS

FIG. 1A is a view schematically illustrating a device configuration example of an object sensor of the present invention in the case where the object sensor is used as a rain sensor. FIG. 1B is a view illustrating light 130 in the case where an object is present on the detection surface. FIG. 1C is a view illustrating light 140 in the case where there is no object on the detection surface.

FIG. 15 is a view schematically illustrating the relationship between the arrangement of the micro-photodetecting elements and raindrops.

FIGS. 16A to 16C are views schematically illustrating a controlling operation in which micro-photodetecting elements are operated at every three positions, and a sampling operation is carried out using these micro-photodetecting elements as a group.

DESCRIPTION OF THE INVENTION

Figure 2A:
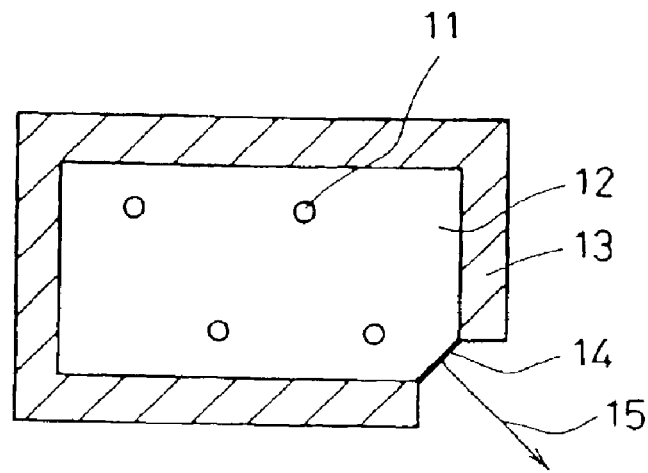
FIG. 2A is a view schematically illustrating an end face of a light source unit 10.

The following will describe embodiments of an object sensor of the present invention and a controller employing the same, while referring to the drawings.

Embodiment 1

Embodiment 1 is a device configuration example of an object sensor of the present invention used as a rain sensor, as an embodiment of an object sensor of the present invention.

FIG. 1A is a view schematically illustrating a device configuration example of a rain sensor. As will be described later in detail, sets of elements are configured in array in Embodiment 1, and FIG. 1A illustrates a cross section corresponding to only one of the foregoing sets. A plurality of sets of the elements shown in FIG. 1A are provided in a direction perpendicular to a surface of a sheet on which FIG. 1A is carried.

In FIG. 1A, 100 denotes a windshield of a vehicle as a transparent substrate. For convenience in description, a space above the windshield 100 indicates the inside of a vehicle, that is, the space on the driver side, and a space below the windshield 100 indicates the outside of the vehicle. 110 denotes an object detection surface, which is on a surface of the windshield 100.

10 denotes a light source section of a linear illumination that is a light-emitting section. 20 denotes a prism for guiding light from the light source into the windshield. 30 denotes a prism for guiding reflected light out of the windshield. 40 denotes a focusing lens that constitutes an optical focusing system between a photodetecting surface of a photodetecting unit and the detection surface. 50 denotes the photodetecting unit including a plurality of micro-photodetecting elements.

The arrangement of the light source section 10, the prism 20, the windshield 100, the detection surface 110, the prism 30, the focusing lens 40, and the photodetecting unit 50, and mounting angles thereof, are selected as shown in FIG. 1A. The arrangement and mounting angle of the foregoing elements are selected so that light emitted from the light source section 10 and guided into the windshield 100 via the prism 20 is incident on the detection surface 110, and that without any object adhering to the detection surface 110, that is, with air in contact therewith, the total internal reflection condition is satisfied on the detection surface. Besides, the arrangement and mounting angle of the foregoing elements are selected so that reflected light that is obtained as a result of the total internal reflection at the detection surface and is directed to the inside of the windshield 100 exits the windshield 100 via the prism 30 mounted on a surface of the windshield 100, and is focused by the focusing lens 40 on photodetecting surfaces of photodetecting elements of the photodetecting unit 50. Furthermore, the arrangement and mounting angle of the foregoing elements are selected so that the total internal reflection condition is satisfied on the detection surface 110 when nothing adheres to the detection surface and air is in contact therewith as shown in FIG. 1C, whereas the total internal reflection condition is not satisfied on the detection surface 110 in the case where a raindrop (moisture) is in contact therewith as shown in FIG. 1B.

The arrangement and mounting angle of the elements will be described in more detail in Embodiment 2.

The total internal reflection condition can be expressed as:

$$\theta_1 > \sin^{-1}\left(\frac{n_1}{n_2}\right) \quad (3)$$

where $n_1$ represents a refractive index of a medium on the outside of the vehicle, $n_2$ represents a refractive index of the windshield 100, and $\theta^1$ represents an incident angle of a beam 140 on the detection surface.

Here, the medium on the outside in the case where no raindrop is present as shown in FIG. 1C has a refractive index of air, that is, a refractive index $n_1$ of 1, and the windshield 100 is assumed to have a refractive index $n_2$ of, for instance, approximately 1.51. Then, 41.47<$\theta_1$ is derived from the foregoing formula (3). Furthermore, in the case where a raindrop adheres thereto as shown in FIG. 1B, $\theta_1$<61.47, preferably is satisfied since water has a refractive index of approximately 1.33. In other words, the incident angle $\theta_1$ is selected so as to fall in a range of 41.47<$\theta_1$<61.74, to ensure the switching between the satisfaction and the failure of the total internal reflection condition expressed as the formula (3) on the detection surface 110. As an example of the arrangement and mounting angle of the elements that satisfy the foregoing condition, the incident angle of the light emitted from the light source section 10 on the detection surface 110 and the reflection angle of the light from the detection surface 110 both are selected to be 47°.

The following will describe the elements shown in FIG. 1A in more detail.

Figure 2B:
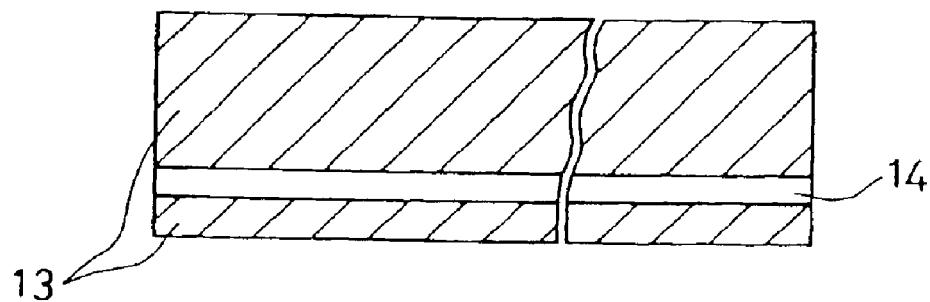
FIG. 2B is a view illustrating the light source unit 10, which is viewed from a side of a surface on which an opening 14 is seen.
Figure 11:
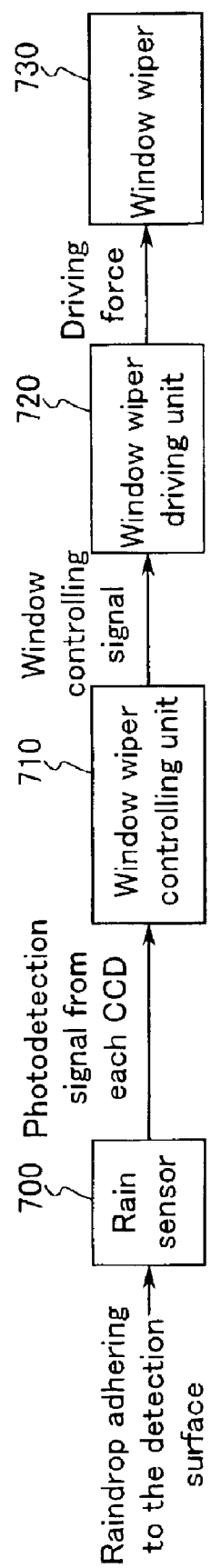
FIG. 11 is a block diagram illustrating a window wiper controller employing the object sensor as a rain sensor.

FIG. 2 is a view schematically illustrating a configuration of the light source section 10. FIG. 2A illustrates an end face of the light source section 10, and FIG. 2B is a view illustrating a surface thereof having an opening 14 as viewed from the front side. In FIGS. 2A and 2B, 11 denotes an LED as a light source, 12 denotes a photoconductor, 13 denotes a cover for blocking light, 14 denotes an opening through which LED light is allowed to exit, and 15 denotes a beam emitted from the LED 11. The light source section 10 includes a light source such as a plurality of LEDs at one or both ends, and is intended to allow light to exit through the linearly-provided opening 14 after repetitive internal reflection on inside surfaces of the cover 13. The LEDs may be arranged on a surface of a glass photoconductor opposite to the opening 14 at uniform intervals. The light source section 10 is arranged at a position and angle such that the beam is incident on the detection surface 110 at a predetermined angle.

The following will describe the study on the size of a raindrop adhering to the windshield 100. Though the size of a raindrop adhering to the windshield 100 significantly varies with the size of a raindrop while falling and the state of adhesion thereon, specific values are assumed as a guide in the following study. Generally, a raindrop of so-called drizzle has a diameter of approximately 0.1 mm to 0.2 mm when falling in air, a raindrop of so-called light rain has a diameter of approximately 0.2 mm to 1 mm when falling in air, a raindrop of so-called heavy rain has a diameter of approximately 2 mm to 4 mm when falling in air, and a raindrop of particularly heavy rain such as shower has a diameter of approximately 4 mm to 6 mm when falling in air. The size of such a raindrop when it adheres to the windshield 100 varies depending on whether the glass surface is hydrophilic or hydrophobic. Assuming that the glass surface is hydrophobic, the raindrop has approximately the same size as that in air when it adheres to the surface. Here, when an average size of raindrops of light rain, for instance, 0.5 mm in diameter, is assumed as the smallest size of raindrops to be detected, an area of a micro-region corresponding to one of the raindrops is approximately 0.2 mm². When the smallest size of raindrops of light rain, 0.2 mm in diameter, is assumed as the smallest size of raindrops to be detected, so as to improve the sensitivity further, an area of a micro-region corresponding to one of the raindrops is approximately 0.03 mm².

Thus, each of the beams guided from the light source section 10 preferably is set to have a cross section with an area not greater than approximately 0.2 mm², more preferably not greater than approximately 0.03 mm².

Figure 3:
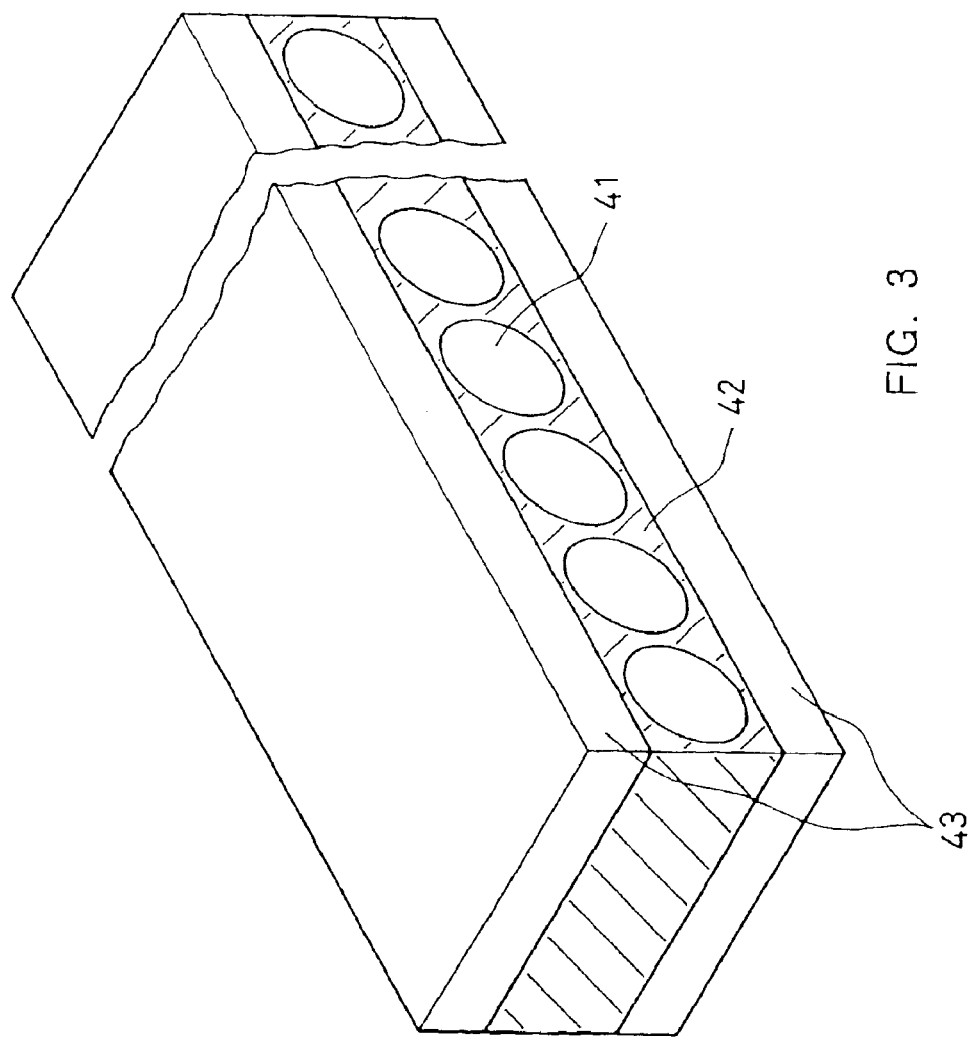
FIG. 3 is a schematic view illustrating an example of the focusing lens 40.

Next, the focusing lens 40 is described in detail. The focusing lens 40 focuses an image of the detection surface on the micro-photodetecting elements of the photodetecting unit 50. The focusing lens 40 and the photodetecting unit 50 are arranged with angles and a distance therebetween selected so that light having been irradiated the detection surface is incident on the focusing lens 40 so as to be focused on the photodetecting unit 50. FIG. 3 is a view schematically illustrating an example of the focusing lens 40. As the focusing lens 40, a graded refractive index lens array can be employed. FIG. 3 schematically illustrates a configuration of a Selfoc Lens Array (SLA: registered trademark), which is a kind of a graded refractive index lens array of equal magnification focusing system. 41 is a rod lens as a microlens, 42 denotes a black resin, and 43 denotes a fiberglass reinforced plastic (FRP) plate. The rod lens 41 has a bar form, whose lens face is seen in FIG. 3. FIG. 1A illustrates a side cross section corresponding to only one of the rod lenses 41. The use of the SLA allows the incident beam to be bent and focused at a predetermined position, thereby allowing an erect image under equal magnification to be formed. In other words, reflected light obtained from a portion of the detection surface 110 can be focused without any change on a corresponding one photodetecting element.

The foregoing example is a case of the rod lenses 41 that are arrayed in a linear form, but the lenses may be arranged in a manner according to the arrangement of micro-beams obtained from the light source section 10 and the arrangement of the photodetecting elements of the photodetecting unit 50, which will be described later. The example shown in FIG. 3 is an SLA corresponding to the example of the light source section 10 that includes the LEDs shown in FIG. 2 arranged in a linear form inside the opening 14.

It should be noted that an example of a focusing system of equal magnification is described in the above, but it is of importance that photodetecting surfaces of the photodetecting elements constituting the photodetecting unit 50 and the detection surface 110 form a focusing optical system.

Figure 4:
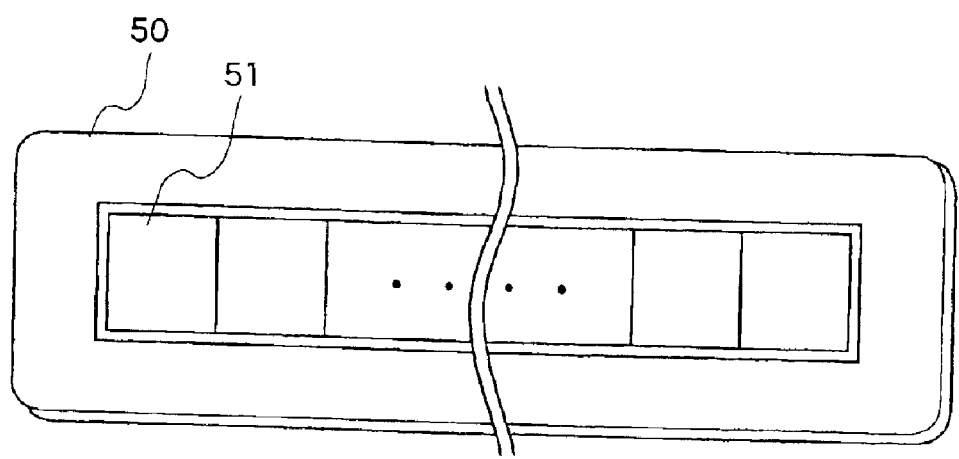
FIG. 4 is a view schematically illustrating an example of the photodetecting unit 50.

The following will describe the photodetecting unit 50 in detail. FIG. 4 is a view schematically illustrating an example of the photodetecting unit 50. In the example shown in FIG. 4, photodetecting elements of the photodetecting unit 50 are arranged in a linear form. 51 denotes a photodetecting element, whose photodetecting surface is illustrated conceptually. It should be noted that the illustration of capacitors, transistor circuits, sense amplifier circuits, etc. that are incorporated inside the photodetecting elements 51 is omitted so that the drawing shows that the photodetecting surfaces of the photodetecting elements 51 are arranged in a linear form. The photodetecting surfaces of the photodetecting elements 51 are arranged so as to correspond to the arrangement of the opening 14 of the light source section 10 and the arrangement of the lenses of the focusing lens 40, and distances and angles thereof are selected so that on each of the photodetecting surfaces of the photodetecting elements 51, reflected light from a corresponding portion of the detection surface 110 is focused via the focusing lens 40.

It should be noted that an effective area of the photodetecting surface of the photodetecting element 51 can be selected according to an area of an object to be detected. In the case where the focusing lens 40 is a focusing system of equal magnification, according to the above-described study on the size of the object to be detected on the detection surface 110, the effective area of the photodetecting surface of the photodetecting element 51 preferably is set to be not more than approximately 0.2 mm$^2$, more preferably not more than approximately 0.03 mm$^2$. However, it is possible to use a photodetecting element having an effective area of a photodetecting surface in a range different from the above range.

The following will describe an operation of the object sensor shown in FIG. 1A, and a principle of detecting an object.

FIG. 1B is a view illustrating a beam in the case where a raindrop as an object adheres to the detection surface 110. FIG. 1C is a view illustrating a beam in the case where no object adheres to the detection surface 110. 120 denotes a raindrop adhering to the detection surface 110, 130 denotes light having been incident on a portion thereof to which the raindrop adheres, and 140 denotes light having been incident on a portion thereof to which no raindrop adheres.

A plurality of beams guided from the light source section 10 to the windshield 100 are incident on the detection surface 110. As shown in FIG. 1C, a beam having been incident on a portion of the detection surface 110 where no raindrop 120 is present is reflected to the inside of the windshield 100, as the beam 140 shown in the drawing, since the total internal reflection condition is satisfied on the detection surface 110 as described above. The reflected light passes through the prism 30, the focusing lens 40, and is received by the photodetecting unit 50. Here, since the light is incident on an entirety of the photodetecting surface of a corresponding photodetecting element 51, a signal value detected by the corresponding photodetecting element 51 is sufficiently great.

On the other hand, a beam incident on a portion of the detection surface 110 on which a raindrop 120 is present as shown in FIG. 1B passes through the windshield 100 and exits to the outside of the vehicle, as the beam 130 shown in the drawing, since the total internal reflection condition is not satisfied on the detection surface 110. Therefore, a photodetecting element 51 of the photodetecting unit 50 corresponding to the portion of the detection surface 110 having the raindrop 120 adhering thereto receives little light, and hence, a signal detected by the corresponding photodetecting element 51 has a sufficiently small value.

Figure 5:
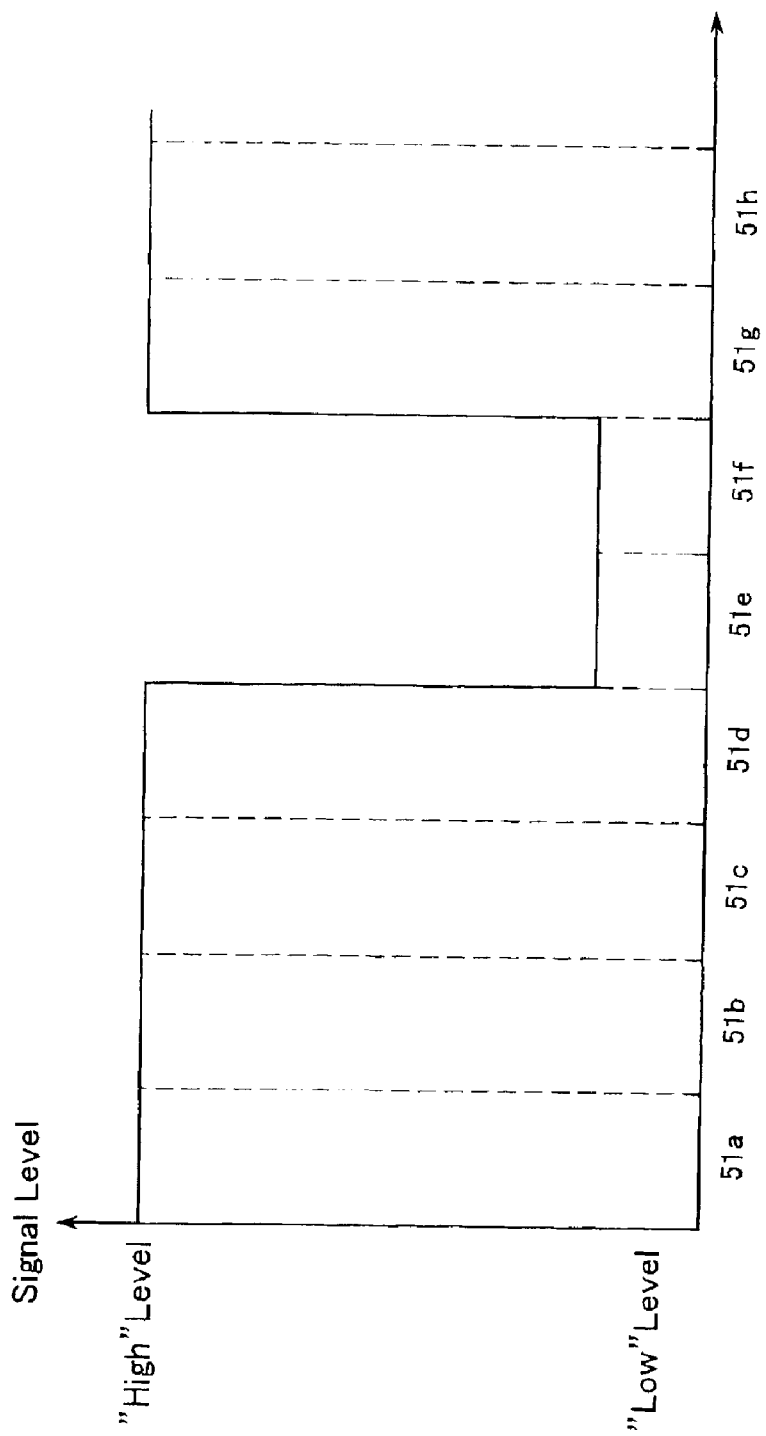
FIG. 5 is a view illustrating a photodetection signal example from photodetecting elements 51 composing the photodetecting unit 50.

FIG. 5 is a view schematically illustrating an example of photodetection signals from photodetecting elements 51 composing the photodetecting unit 50. In FIG. 5, photodetection signals obtained from eight photodetecting elements 51*a* to 51*h* are shown. The photodetection signals obtained from six photodetecting elements 51*a* to 51*d*, 51*g*, and 51*h* have relative values that are sufficiently great, while the photodetection signals obtained from the photodetecting elements 51*e* and 51*f* have relative values that are sufficiently small. In other words, the following is presumed. A raindrop is present on a portion of the detection surface 110 to be detected by the photodetecting element 51*f*, whereby the total internal reflection condition expressed as the formula (3) is not satisfied. This causes the incident light to exit to the outside of the vehicle, as the beam 130 shown in FIG. 1B. Therefore, the beam is not received, and the photodetection signal level lowers. As shown in FIG. 5, a photodetection signal from each of the photodetecting elements 51 appears clearly at either a "high" level or a "low" level digitally, and the presence or absence of an object on the detection surface 110 can be detected surely. In other words, it is possible to detect the presence or absence of an object on the detection surface 110 with a high sensitivity.

It should be noted that by taking advantage of the clear appearance of the photodetection signal from each photodetecting element 51 at either a "high" level or a "low" level in a digital manner, it is possible to make the determination by setting an appropriate threshold on the photodetection signal. Furthermore, it also is possible to digitalize each of the photodetection signals from the photodetecting elements 51 by utilizing a finite difference value as a reference, the finite difference value being a decrease from a photodetection signal level as a reference.

Furthermore, it is possible to generate a signal pattern (waveform) in which the photodetection signals from the photodetecting elements 51 are arranged according to the arrangement of the photodetecting elements 51. The signal pattern is a pattern obtained by linking the levels of the photodetection signals obtained from the detection surface, and the variation of a state of an object on the detection surface appears as relative variances in micro-domains in the signal pattern. In the present invention, there is no need to analyzing absolute values of signal levels, and it is possible to detect an increase in an amount of external light incident from the outside with high precision by analyze relative variances in the signal pattern, that is, a change in the waveform.

Figure 6:
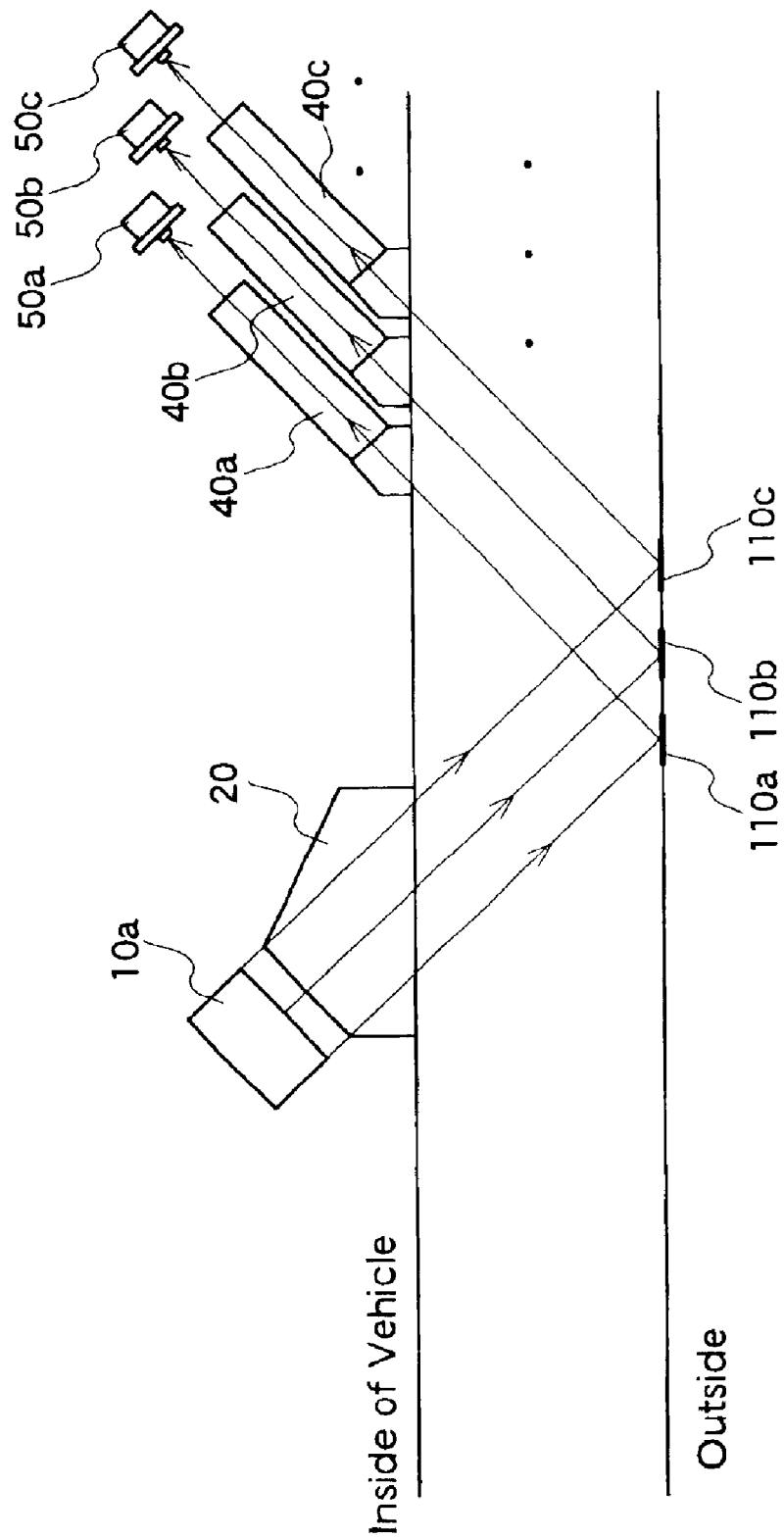
FIG. 6 is a view illustrating a configuration in which a plurality of elements of the object sensor shown in FIG. 1 are arranged in a direction parallel with a surface of the sheet carrying the drawing.
Figure 7A:
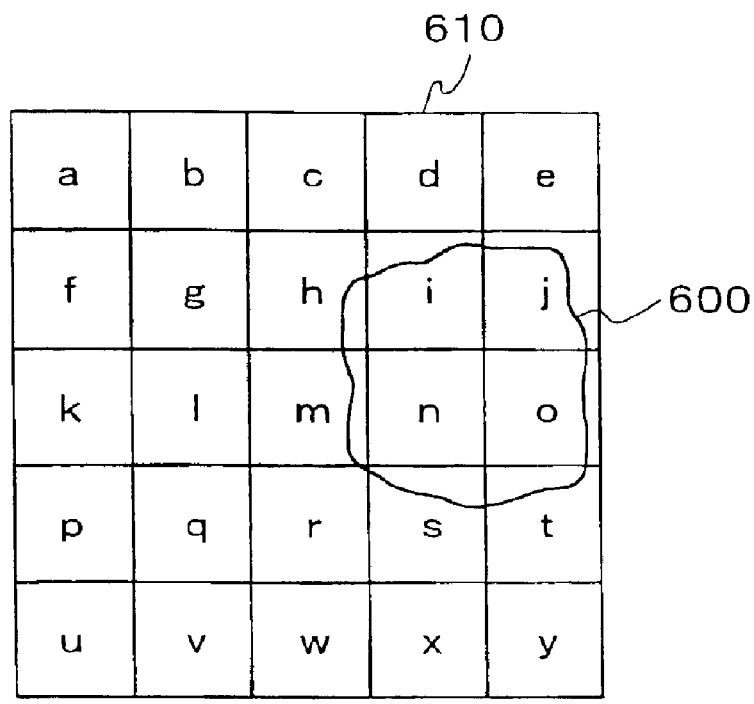
FIG. 7A is a view illustrating the relationship between a detection surface 110 and an object.
Figure 7B:
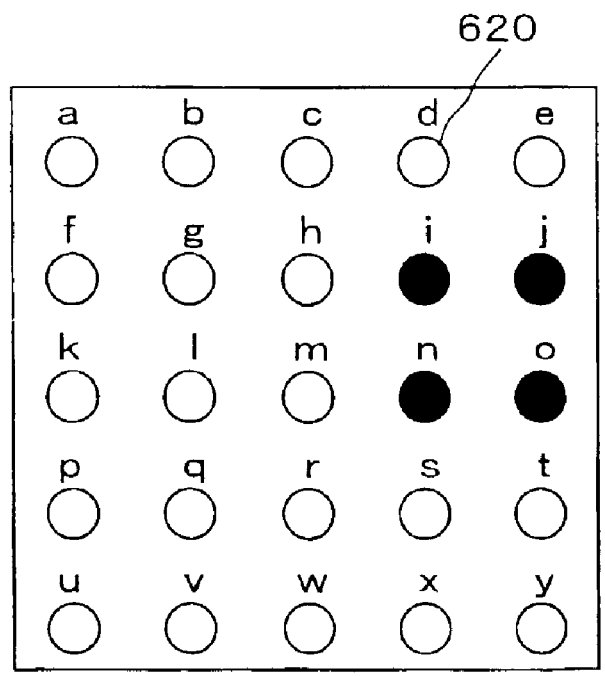
FIG. 7B is a view schematically illustrating a photodetection signal value detected by the photodetecting elements.

Furthermore, by analyzing the digital signal or the signal pattern with the arrangement of the photodetecting elements 51 taken into consideration, an approximate size and shape of an object adhering to the detection surface 110 can be estimated. FIG. 6 is a view illustrating a configuration in which the elements of the object sensor shown in FIG. 1A are arranged in array, here, also in a direction parallel with a surface of a sheet on which FIG. 6 is carried. Since the sets of elements are arranged in array also in the direction perpendicular to the surface of the sheet as described in conjunction with FIG. 1A, the sets of elements consequently are arranged two-dimensionally in the configuration shown in FIG. 6. FIGS. 7A and 7B are views conceptually illustrating a principle for estimating an approximate size and shape of an object adhering to the detections surface 110. FIG. 7A is a view illustrating the relationship between the detection surface 110 and an object adhering to the detection surface 110. FIG. 7B is a view conceptually illustrating digitalized photodetection signals obtained from the photodetecting elements corresponding to respective portions of the detection surfaces 110, the photodetection signals being arranged according to the arrangement of the photodetecting elements. In FIG. 7A, 600 denotes a raindrop as the object, and 610*a* to 610*y* denote twenty five micro-domains, respectively. The raindrop 600 and the micro-domains 610*a* to

610y are in the relationship shown in the drawing, in which the raindrop 600 substantially covers four micro-domains 610i, 610j, 610n, and 610o. FIG. 7B schematically illustrates photodetection signals of photodetecting elements 620a to 620y that are arranged so as to correspond to the micro-domains 610a to 610y, respectively, according to the arrangement of the photodetecting elements. A void circle indicates that a value of a signal of the photodetecting element is at a "high" level, while a solid circle indicates that a value of a signal of the photodetecting element is at a "low" level. In this example, photodetection signals of the four photodetecting elements 620i, 620j, 620n, and 620o are at the "low" level. From the result shown in FIG. 7B, it is seen, though roughly, that it is possible to estimate to some extent that the raindrop adhering to the detection surface has a size such that it substantially covers four micro-domains 610, and has a shape such that a vertical dimension and a horizontal dimension thereof are substantially equal, that is, a shape approximate to a circle or a square.

In the case where the object is a raindrop, it further is possible to estimate to some extent whether the rain is drizzle, light rain, or heavy rain from the estimated size of the raindrop. Generally, a greater raindrop falls at a higher speed, thereby adhering to a region with a greater area. Furthermore, generally, with a greater size of a raindrop, it can be estimated that an amount of rainfall is greater. Therefore, it is possible to select the operating frequency of a wiper according to the detected size of the raindrop. For instance, a plurality of threshold values may be provided for classifying the sizes of the adhering raindrop, and it is checked in which class a detected size of a raindrop is classified. For instance, two threshold values may be set, and in the case where the size is not greater than the smaller threshold value, it is classified as "drizzle". In the case where it is greater than the smaller threshold value and not greater than the greater threshold value, it is classified as "light rain". In the case where it is greater than the greater threshold value, it is classified as "heavy rain". Thus, the classification into the "drizzle", "light rain", and "heavy rain" classes is ensured.

Likewise, the type of rainfall also can be estimated referring to the ratio of the signals at the "low" level to the entire photodetection signals of the photodetecting elements, instead of or in combination with the size of a raindrop. In the case where an amount of rain increases, the number of raindrops that fall during a certain set time increases also, thereby increasing a ratio of adhesion of raindrops to the detection surface. Therefore, by monitoring the number of signals at the "low" level detected per a unit time, the number of raindrops per a unit time can be estimated, and further, the type of rainfall can be estimated.

The example shown in FIG. 7 is a case in which the shape and type of an object is estimated by analyzing digitalized photodetection signals, but it is possible to estimate the shape and type of an object by analyzing a signal pattern obtained by linking signal values.

The object sensor described above as Embodiment 1 is a mere example, and the object sensor of the present invention is not limited to the above-described specific device configuration example. It may be configured in another manner based on the technological idea of the present invention, and may be used for purposes other than the rain sensor.

Embodiment 2

In Embodiment 2, elements and mounting angles thereof, etc., will be described in detail, with reference to a case in which an object sensor of the present invention is used as a rain sensor.

In the object sensor of the present invention as a rain sensor, a mounting angle of a light-emitting means, an angular aperture of a focusing lens, a mounting angle of the focusing lens, etc. are selected so as to satisfy the requirements described below, in order to determine the presence/absence of an object such as raindrops with a high sensitivity.

The first requirement is that, in order to eliminate influences of external light as noise, the mounting angle of the light-emitting means, the angular aperture of the focusing lens, and the mounting angle of the focusing lens have to be selected so that external light should not directly enter the photodetecting elements of the rain sensor. This is a requirement for solving the problem mentioned as the aforementioned first matter.

Here, the elements are arranged with the angular aperture and the mounting angle of the focusing lens, which are mentioned as the third matter to be studied, also taken into consideration.

The second requirement is that an incident angle of light from the light-emitting means to the detection surface and a refractive index of a transparent substrate have to be selected so that the satisfaction and the failure of the total internal reflection condition on the detection surface are switched therebetween according to the presence/absence of an object. This is a requirement for solving the problem mentioned as the aforementioned second matter.

The third requirement is that, in order to reduce light loss of the transparent substrate such as a windshield, the mounting angle of the light-emitting means, the angular aperture of the focusing lens, and the mounting angle of the focusing lens have to be selected so that an optical path inside the transparent substrate is minimized in length. This is a requirement for solving the problem mentioned as the aforementioned fourth matter.

First, the first requirement is discussed, which is the selection of the mounting angle of the light-emitting means, the angular aperture of the focusing lens, and the mounting angle of the focusing lens that avoid direct incidence of external light on the photodetecting elements of the rain sensor.

Figure 8:
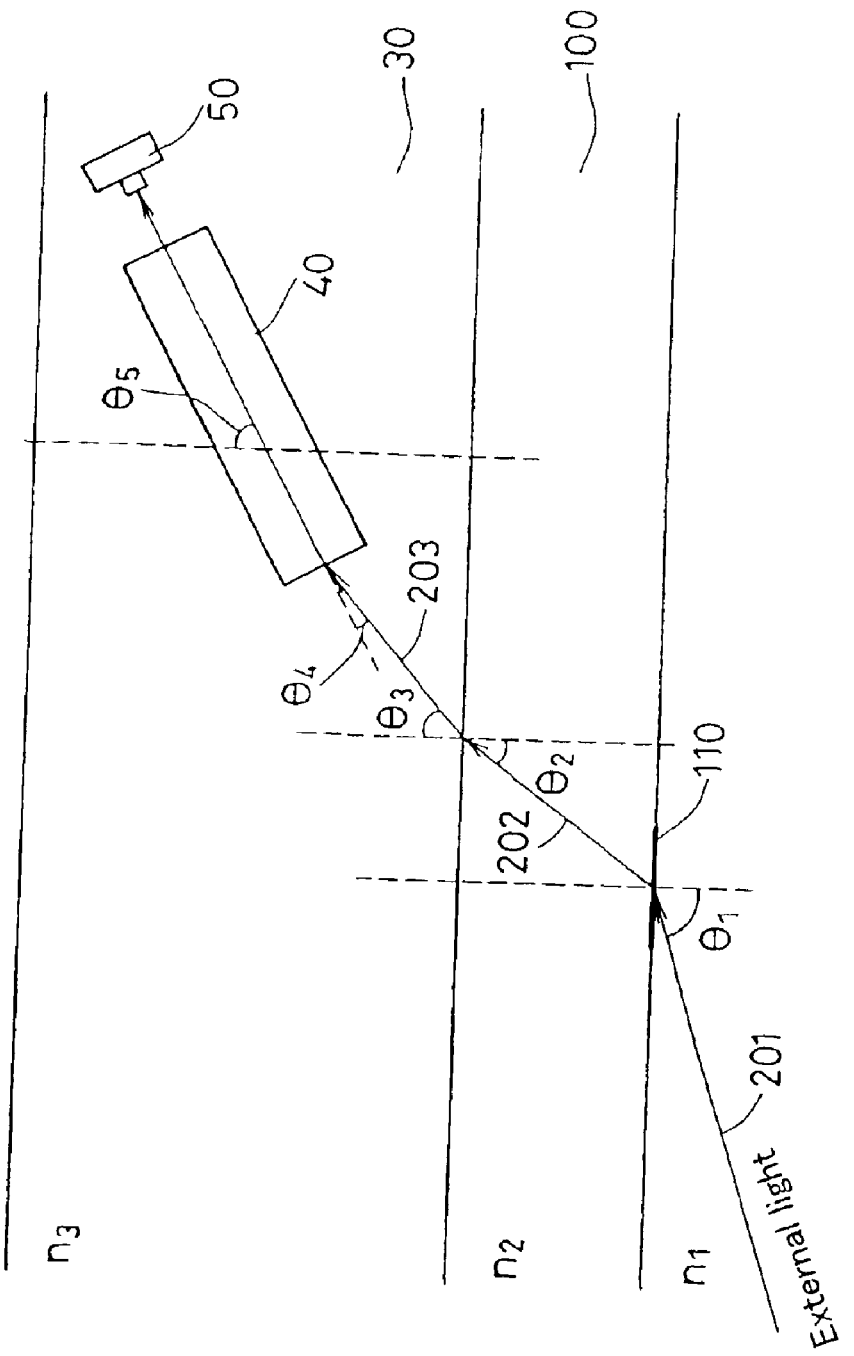
FIG. 8 is a view schematically illustrating a path of external light incident from outside, in the object sensor of the present invention.

FIG. 8 is a schematic cross-sectional view of the object sensor of the present invention that conceptually and simply illustrates a path of external light in the case where external light from the outside is incident and is received by a photodetecting element in the object sensor of the present invention. The drawing shows the optical path along which light refracted on the detection surface or the like after entrance travels until it is received by the photodetecting element, the mounting angles of the elements of the device, and the materials thereof. It should be noted that FIG. 8 is intended to find the requirement for preventing external light from being received, by analyzing critical conditions under which external light is received. Therefore, it is not intended to show a configuration example. A view schematically illustrating configuration example of the object sensor of the present invention is FIG. 9.

In FIG. 8, three layers are shown. The lower layer denotes the outside of the vehicle, the middle layer denotes the windshield 100 of the vehicle as a transparent substrate, and the upper layer denotes a contact medium layer 30 as a prism that fills a space between the windshield 100 and the focusing lens 40 so as to bring the both into contact with each other. The space on the upper side of the windshield 100 is the inside of the vehicle, that is, the space on the driver side, while the space on the lower side thereof is the outside of the vehicle on the front side. A detection surface 110 is provided in a certain set area on an interface between the windshield 100 and the outside. It should be noted that 40 denotes the focusing lens, and 50 denotes the photodetecting element of the photodetecting means.

Here, it is assumed that a refractive index of the outside is $n_1$, a refractive index of the windshield 100 is $n_2$, and a refractive index of the contact medium layer 30 is $n_3$.

Tracing the path of external light in the case where it directly enters the photodetecting element 50, it is incident on the detection surface 110 at an incident angle $\theta_1$ from the outside (this light is denoted as 201), is refracted at an interface with the windshield 100 with an angle of refraction $\theta_2$ (this refracted light is denoted as 202), and passes through the windshield 100. Next, the light 202 is refracted further at an interface between the windshield 100 and the contact medium layer 30 at an angle of refraction $\theta_3$ (this light is denoted as 203) and travels inside the contact medium layer. The light 203 is incident on the focusing lens 40 at an incident angle $\theta_4$. It is assumed that a mounting angle of the focusing lens, that is, an angle formed between an optical axis of the lens 40 and the normal of the windshield 100, is $\theta_5$. Here, the focusing lens has an angular aperture $\theta_S$, and as will be described later, in the case where the refractive index $n_3$ of the contact medium layer 30 and the incident angle $\theta_4$ satisfy a certain relationship, the light 203 incident at the incident angle $\theta_4$ is converged, passes through the focusing lens 40 (this light is denoted as 204) in a direction such that an angle formed between its optical path and the normal of the windshield 100 is $\theta_5$, and is received by the photodetecting element 50.

Therefore, to find the requirement for avoiding direct incidence of external light on a photodetecting element of a rain sensor, conditions that cause light not to travel along the above-described path may be analyzed.

First of all, a maximum possible angle as the incident angle $\theta_1$ when light is incident on the detection surface 110 is 90°.

$$\theta_1 \leq 90° \quad (4)$$

Next, the relationship between angles is sorted out as described below.

The relationship between the light 201 and the light 202 at the detection surface 110, that is, an interface between the outside and the windshield 100 is expressed as a formula (5) as follows.

$$n_1 \sin \theta_1 = n_2 \sin \theta_2 \quad (5)$$

Furthermore, the relationship between the light 202 and the light 203 at an interface between the windshield 100 and the contact medium layer 30 can be expressed as a formula (6) as follows:

$$n_2 \sin \theta_2 = n_3 \sin \theta_3 \quad (6)$$

Furthermore, the relationship between the light 203 and the light 204 can be expressed as a formula (7) shown below, from the light conversion relationship between the contact medium layer 30 and the focusing lens 40:

$$\theta_3 + \theta_4 = \theta_5 \quad (7)$$

Since external light does not directly enter the photodetecting element of the rain sensor when the value on the left part in the foregoing formula (7) is smaller than $\theta_5$, a formula (8) described below can be derived from the relationships of the formulae (5) to (7).

$$\sin^{-1}\left(\frac{n_1}{n_3}\right) + \theta_4 < \theta_5 \quad (8)$$

Here, the relationship between the incident angle $\theta_4$ to the focusing lens 40 and the angular aperture $\theta_S$ of the focusing lens 40 is expressed by the following formula (9):

$$\theta_S = n_3 \times \theta_4 \quad (9)$$

From the formulae (8) and (9), the condition under which external light does not enter the photodetecting element of the rain sensor directly is expressed by the following formula (1):

$$\sin^{-1}\left(\frac{n_1}{n_3}\right) + \left(\frac{\theta_S}{n_3}\right) < \theta_5 \quad (1)$$

It should be noted that the outside of the windshield 100 is air, and hence it has a refractive index $n_1$ of 1.

The boundary condition, as expressed by the formula (1), is described in more detail below, with specific numerical values taken as examples. Examples of a material forming the contact medium layer 30 are silicone, glass, and polycarbonate, which have refractive indices $n_3$ of 1.41, 1.51, and 1.59, respectively. Table 1 below shows the relationship between the angular aperture $\theta_S$ and the mounting angle $\theta_5$ of the focusing lens 40, with $n_3$ used as a parameter.

TABLE 1

| Lens Array | Mounting angle of Lens Array $\theta_5$ (deg.) | | |
|---|---|---|---|
| Angular Aperture $\theta_S$ (deg.) | Silicone $n_3 = 1.41$ | Glass $n_3 = 1.51$ | Polycarbonate $n_3 = 1.59$ |
| 4 | 48.01 | 44.12 | 41.49 |
| 6 | 49.43 | 45.45 | 42.74 |
| 9 | 51.55 | 47.43 | 44.63 |
| 12 | 53.68 | 49.42 | 46.52 |
| 15 | 55.81 | 51.41 | 48.41 |
| 20 | 59.36 | 54.72 | 51.55 |

In Table 1, as the condition under which external light does not enter the photodetecting element of the rain sensor directly, acceptable minimum mounting angles $\theta_5$ of the focusing lens 40 are shown in the right three columns, regarding each combination of angular apertures $\theta_S$ of the focusing lens 40 shown in the left column and materials of the contact medium layer 30.

The focusing lens 40 tends more to allow external light to enter itself as an angle formed between its optical axis and the windshield is closer to a right angle, and it allows external light to directly enter itself if it is mounted so that the mounting angle is not more than the degrees shown in Table 1, for instance.

Thus, consequently, regarding the first requirement, in the case where the mounting angle $\theta_5$ is greater than the degrees shown in Table 1, external light does not directly enter the photodetecting element of the rain sensor.

Next, the following will describe the second requirement, that is, the selection of an incident angle of light from the light-emitting means to the detection surface and a refractive index of a transparent substrate such that the satisfaction and the failure of the total internal reflection condition on the detection surface are switched therebetween according to the presence/absence of an object.

Figure 9:
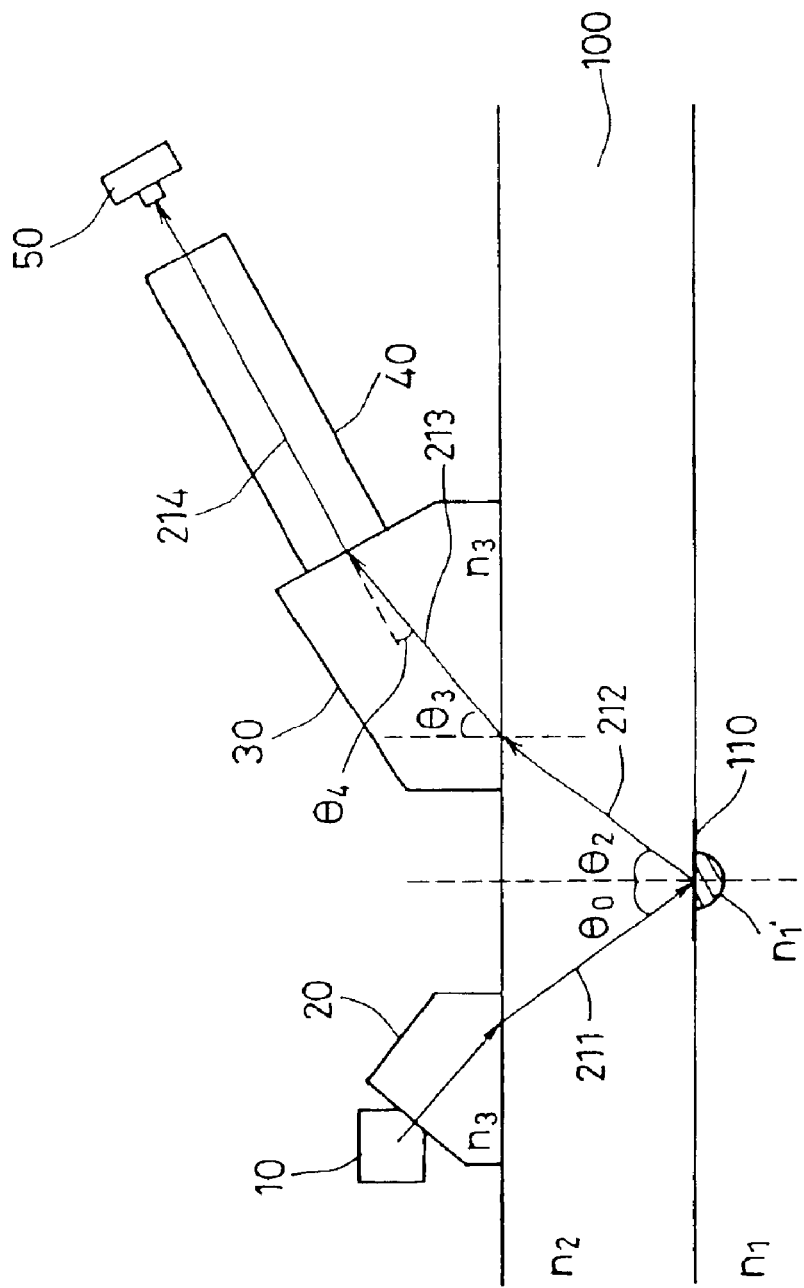
FIG. 9 is a view illustrating a path of light from the light-emitting means that is incident on the detection surface and reflected thereby entering the photodetecting element, as well as mounting angles and materials of the device elements, in the object sensor of the present invention.

FIG. 9 illustrates a path of light emitted by the light-emitting means, incident on the detection surface, and reflected therefrom in the object sensor of the present invention. The drawing indicates the path of the light until it reaches the photodetecting element, as well as the mounting angles and materials of device elements.

Three layers shown in FIG. 9, that is, the outside of the vehicle, the windshield 100, and the contact medium layer 30 are identical to those shown in FIG. 8. Besides, the same reference numerals of the elements, and the same materials of the elements (refractive indices) as those in FIG. 8 are used as long as it is possible.

10 denotes a light-emitting means. Tracing the path of light emitted from the light-emitting means 10, the light emitted from the light-emitting means 10 is incident on the detection surface 110 at an incident angle $\theta_0$ (this light is denoted as 211), and is subjected to the total internal reflection on the detection surface in the case where no object is present on the detection surface 110, thereby being reflected inside the windshield 100 (this light is denoted as 212). Since a part of the results of the analysis regarding the first requirement is used herein regarding an angle of the foregoing reflection, this reflection angle at which the light is reflected so as to travel through the windshield 100 is denoted as $\theta_2$ for convenience sake. The light 212 further is refracted at an interface between the windshield 100 and the contact medium layer 30 at an angle of refraction $\theta_3$, and travels inside the contact medium layer (this light is denoted as 213). The light 213 is incident on the focusing lens 40 at an incident angle $\theta_4$. A mounting angle of the focusing lens 40, that is, an angle formed between a normal of the windshield 100 and the optical axis of the focusing lens 40, is referred to as $\theta_5$. Here, the focusing lens 40 has an angular aperture $\theta_S$, and when a refractive index $n_3$ of the contact medium layer 30 and the incident angle $\theta_4$ satisfy a certain relationship, the light 213 incident at the incident angle $\theta_4$ is converged, passes through the focusing lens 40 in a direction such that an angle formed between the light traveling direction and the normal of the windshield 100 is $\theta_5$ (this light is denoted as 214) and is received by the photodetecting element 50.

First of all, if there is no adhering object, the following formula (10) has to be satisfied so that the total internal reflection condition is satisfied at the detection surface 110.

$$\sin^{-1}\left(\frac{n_1}{n_3}\right) < \theta_2 \tag{10}$$

If there is no object on the windshield 100, which means that the detection surface is in contact with air in the outside, the refractive index $n_1$ is 1. In the case where the windshield 100 made of glass is assumed to have a refractive index $n_2$ of 1.51, 41.47°<$\theta_2$ is derived.

Next, in order that the total internal reflection is not satisfied on the detection surface 110 when there is an adhering object thereon, the following formula (11) has to be established.

$$\theta_2 < \sin^{-1}\left(\frac{n_1'}{n_3}\right) \tag{11}$$

where $n_1'$ represents a refractive index of the object.

Here, if there is a raindrop as an object adhering to the windshield 100, that is, the detection surface is in contact with the raindrop, the refractive index $n_1'$ is 1.33. In the case where the windshield 100 is assumed to have a refractive index $n_2$ of 1.51, $\theta_2$<61.74° is derived.

From the foregoing, the condition under which the satisfaction and the failure of the total internal reflection condition on the detection surface is switched therebetween according to the presence/absence of an object is expressed as the formula (2) shown below:

$$\sin^{-1}\left(\frac{n_1}{n_3}\right) < \theta_2 < \sin^{-1}\left(\frac{n_1'}{n_3}\right) \tag{2}$$

With specific values given to the formula (2), the following formula (12) is derived therefrom.

$$41.47 < \theta_2 < 61.74 \tag{12}$$

Next, the relationship between the light 212 and the light 213 at the interface between the windshield 100 and the contact medium layer 30 is expressed as the following formula (13), which is obtained by modifying the formula (6) described in conjunction with the first requirement.

$$\theta_3 = \sin^{-1}\left(\frac{n_2 \sin\theta_2}{n_3}\right) \tag{13}$$

The boundary condition expressed by the formula (13) is described below with specific values. Examples of a material forming the contact medium layer 30 are silicone, glass, and polycarbonate, whose refractive indices $n_3$ are 1.41, 1.51, and 1.59, respectively. Table 2 below shows the relationship between the reflection angle $\theta_2$ at the detection surface 110 and the incident angle $\theta_3$ on the contact medium layer 30, with $n_3$ used as a parameter.

TABLE 2

| Incident Angle $\theta_2$ (deg.) | Angle of Refraction $\theta_3$ (deg.) | | |
|---|---|---|---|
| | Silicone $n_3$ = 1.41 | Glass $n_3$ = 1.51 | Polycarbonate $n_3$ = 1.59 |
| 41.47 | 45.17 | 41.47 | 38.97 |
| 51.61 | 57.17 | 51.61 | 48.10 |
| 61.74 | 70.61 | 61.74 | 56.77 |

Furthermore, Table 3 below shows examples with specific values of the relationship between the angular aperture $\theta_S$ of the focusing lens 40 and the incident angle $\theta_4$ of the light 213, which is expressed by the formula (9), with $n_3$ used as a parameter.

TABLE 3

| Lens Array | Incident Angle of Lens Array $\theta_4$ (deg.) | | |
|---|---|---|---|
| Angular Aperture θs (deg.) | Silicone $n_3$ = 1.41 | Glass $n_3$ = 1.51 | Polycarbonate $n_3$ = 1.59 |
| 4 | 2.84 | 2.65 | 2.52 |
| 6 | 4.26 | 3.97 | 3.77 |
| 9 | 6.38 | 5.96 | 5.66 |
| 12 | 8.51 | 7.95 | 7.55 |
| 15 | 10.64 | 9.93 | 9.43 |
| 20 | 14.18 | 13.25 | 12.58 |

Since the range of $\theta_2$ is given by the formulae (2) and (12), the relationship between the angular aperture $\theta_S$ and the angle $\theta_5$ is derived from Table 2 showing the relationship between the angles $\theta_2$ and $\theta_3$, the formula (7) expressing the relationship between the angles $\theta_3$, $\theta_4$, and $\theta_5$, and Table 3 showing the relationship between the angular aperture $\theta_S$ and the angle $\theta_4$. Table 4 shows the relationship between the angular aperture $\theta_S$ and the angle $\theta_5$, with $n_3$ used as a parameter.

TABLE 4

| Lens Array Angular Aperture | Mounting angle of Lens Array $\theta_5$ (deg.) | | | | | |
|---|---|---|---|---|---|---|
| | Silicone $n_3 = 1.41$ | | Glass $n_3 = 1.51$ | | Polycarbonate $n_3 = 1.59$ | |
| $\theta s$ (deg.) | Min. | Max. | Min. | Max. | Min. | Max. |
| 4 | 48.01 | 67.77 | 44.12 | 59.09 | 41.49 | 54.26 |
| 6 | 49.43 | 66.35 | 45.44 | 57.77 | 42.74 | 53.00 |
| 9 | 51.55 | 64.23 | 47.43 | 55.78 | 44.63 | 51.11 |
| 12 | 53.68 | 62.10 | 49.42 | 53.79 | 46.52 | 49.22 |
| 15 | 55.81 | 59.97 | 51.40 | 51.81 | 48.40 | 47.34 |
| 20 | 59.36 | 56.42 | 54.72 | 48.49 | 51.55 | 44.19 |

Thus, the conclusion of the analysis of the second requirement is that in the case where the mounting angle $\theta_5$ of the focusing lens 40 is in the range shown in Table 4 (boundary values exclusive), the light emitted from the light-emitting means 10 is received by the photodetecting element 50 when there is no raindrop adhering to the detection surface 110, and it is not received by the same when there is a raindrop adhering thereto.

Next, the following will analyze a range that satisfies both the first and second requirements discussed above at the same time.

Figure 10A:
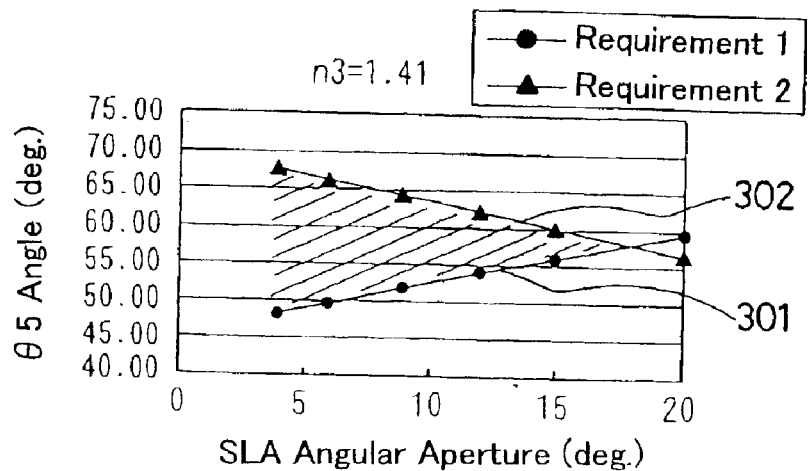
FIGS. 10A to 10C are views illustrating a result of plotting examples of numerical values concerning the first requirement shown in Table 1 and examples of numerical values concerning the second requirement shown in Table 4 on the same graph.
Figure 10B:
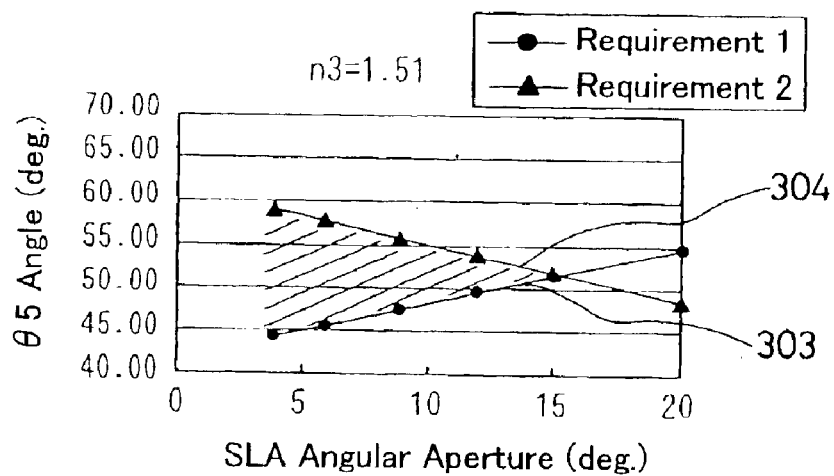
Figure 10C:
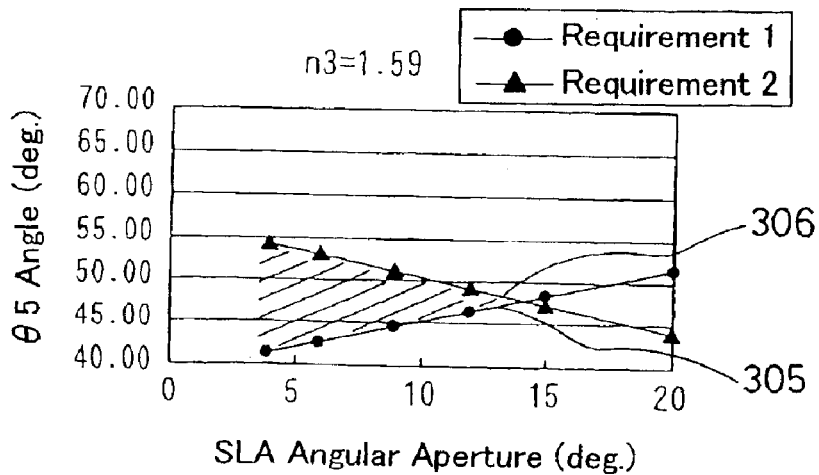

FIGS. 10A to 10C are graphs obtained by plotting both specific examples concerning the first requirement shown in Table 1 and specific example concerning the second requirement shown in Table 4 together.

FIG. 10A is a graph in the case where the contact medium layer 30 is made of silicone (refractive index $n_3=1.41$). 301 denotes a boundary for the first requirement, and 302 denotes a boundary for the second requirement. The first requirement is satisfied when $\theta_5$ is in a range greater than 301, and the second requirement is satisfied when $\theta_S$ is in a range smaller than 302. In other words, a range satisfying the first and second requirements both at the same time is a range shown by hatching with oblique lines. The angular aperture $\theta_S$ substantially has to be not greater than 18°. In other words, in the case where the contact medium layer 30 is made of silicone, a focusing lens 40 having an angular aperture $\theta_S$ of not greater than 18° may be used, and the mounting angle $\theta_5$ of the focusing lens may be selected according to the selected angular aperture $\theta_S$ thereof.

Next, FIG. 10B is a graph in the case where the contact medium layer 30 is made of glass (refractive index $n_3=1.51$). Likewise, 303 denotes a boundary for the first requirement, and 304 denotes a boundary for the second requirement. A range satisfying the first and second requirements both at the same time is a range shown by hatching with oblique lines. The angular aperture $\theta_S$ substantially has to be not greater than 15°. In other words, in the case where the contact medium layer 30 is made of silicone, a focusing lens 40 having an angular aperture $\theta_S$ not greater than 15° may be used, and the mounting angle $\theta_5$ of the focusing lens may be selected according to the selected angular aperture $\theta_S$ thereof.

FIG. 10C is a graph in the case where the contact medium layer is made of polycarbonate (refractive index $n_3=1.59$). Likewise, 305 denotes a boundary for the first requirement, and 306 denotes a boundary for the second requirement. A range satisfying the first and second requirements both at the same time is a range shown by hatching with oblique lines.

The angular aperture $\theta_S$ substantially has to be not greater than 14°. In other words, in the case where the contact medium layer 30 is made of silicone, a focusing lens 40 having an angular aperture $\theta_S$ not greater than 14° may be used, and the mounting angle $\theta_5$ of the focusing lens may be selected according to the selected angular aperture $\theta_S$ thereof.

As described above, based on the foregoing analysis, the object sensor of the present invention is configured as follows. The light-emitting means, the transparent substrate, the focusing optical system, and the photodetecting means are arranged so that reflected light of light emitted from the light-emitting means, which is reflected at the detection surface, can be received by the photodetecting means in the case where there is no object adhering to the detection surface. Mounting angles of the light-emitting means, the transparent substrate, the focusing optical system, and the photodetecting means are selected according to refractive indices of materials present along a path from the outside to the photodetecting means so that external light entering the transparent substrate through an outside surface thereof should not be received directly by the photodetecting means.

Next, the third requirement is described, which is the selection of a mounting angle of the light-emitting means 10, an angular aperture $\theta_S$ of the focusing lens 40, and a mounting angle $\theta_5$ of the focusing lens 40 so that an optical path inside the transparent substrate is minimized in length so as to reduce light loss of the transparent substrate such as a windshield.

As is clear from FIGS. 10A to 10C, in order to minimize in length the optical paths of the lights 211 and 212 passing through the windshield 100, the incident angle $\theta_0$ and the reflection angle $\theta_2$ may be selected so that they are decreased as much as possible. Minimizing $\theta_2$ means decreasing the angle of refraction $\theta_3$ upon the entry of light into the contact medium layer 30 as much as possible, and increasing the incident angle $\theta_4$ upon the incidence on the focusing lens 40 as much as possible. Consequently, it means selecting the mounting angle $\theta_5$ of the focusing lens 40 so that it decreases as much as possible.

More specifically, in the respective drawings of FIGS. 10A to 10C, as to each focusing lens 40 having an angular aperture $\theta_5$ selected, the mounting angle $\theta_5$ of the focusing lens 40 may be selected so as to be decreased, that is, in the ranges shown with the hatching, an angle in a range close to the boundaries 301, 303, and 305 of the first requirement may be selected as the mounting angle $\theta_5$. However, in the actual mounting, margins may be taken into consideration, such as variation of refractive indices of materials, mounting errors in the mounting operations, etc.

Thus, by selecting the mounting angle $\theta_5$ of the focusing lens 40, the optical path passing through the windshield 100 is shortened, so that the light loss occurring in the windshield 100 can be decreased as much as possible.

Embodiment 3

Embodiment 3 describes an example of a configuration of a window wiper controller employing an object sensor as a rain sensor, as an embodiment of a controller employing an object sensor of the present invention.

Figure 12:
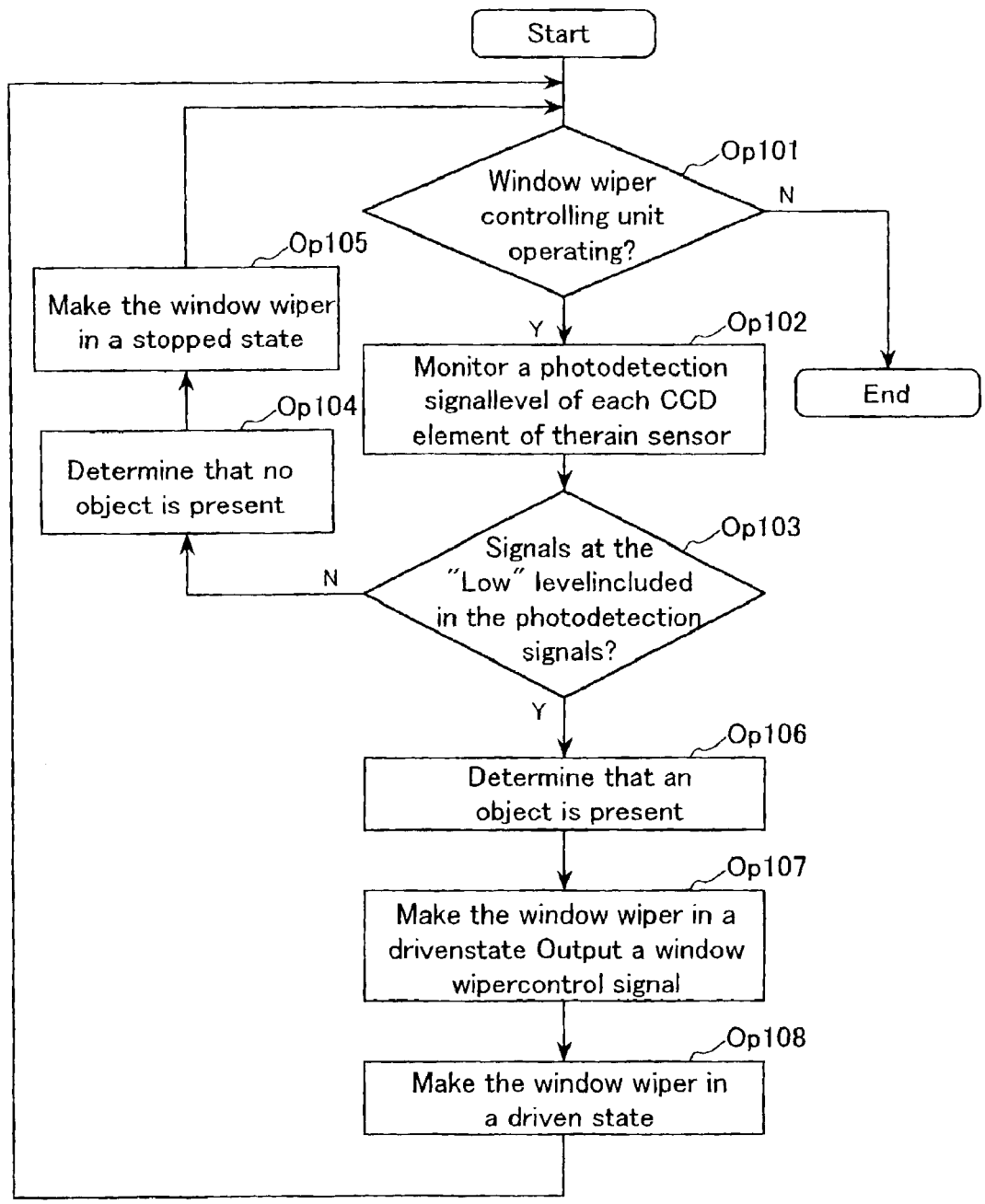
FIG. 12 is a flowchart illustrating an example of a flow of an operation of the window wiper controller of Embodiment 2.

FIG. 11 is an example of a block diagram of a window wiper controller employing an object sensor as a rain sensor. 700 denotes a functional block of a rain sensor as an object sensor of the present invention described in Embodiment 1. 710 denotes a window wiper controlling unit. 720 denotes a window wiper driving unit. 730 denotes a window wiper. These are connected as shown in the drawing. FIG. 12 is a flowchart showing an example of a flow of a processing operation of the window wiper controller of Embodiment 3.

The rain sensor 700, as described in Embodiment 1, senses raindrops of rainfall as objects to be sensed, and outputs a photodetection signal from each photodetecting element. As described in Embodiment 1, a photodetection signal from a photodetecting element corresponding to a portion of the detection surface on which no raindrop is present is at a high level, while a photodetection signal from a photodetecting element corresponding to a portion of the detection surface on which a raindrop is present is at a low level. These signal values can be treated as digital signals, each having either one of binarized values of "high" or "low". Thus, by determining whether a photodetection signal having a "low" value is included or not, it is possible to determine whether there is an object adhering to the detection surface on the windshield.

The window wiper controlling unit 710 receives photodetection signals from the photodetecting elements of the rain sensor 700. In the case where a photodetection signal having a "low" value is included in the photodetection signals, the window wiper controlling unit 710 presumes that there is a raindrop on the windshield, that is, rainfall has started, and transmits a wiper control signal to the window wiper driving unit 720.

Here, applied functions associated with the output of the wiper control signal are described. They include not only a function of detecting the presence of raindrops but also a function of presuming which type of rainfall occurs and changing the content of the wiper control signal according to the type of rainfall. Since the raindrop sensor of the present invention is capable of presuming the size of adhering raindrops and the type of rainfall as described in Embodiment 1, the raindrop sensor is capable of presuming the rainfall state, such as "drizzle", "light rain", or "heavy rain" based on the size of the raindrops, and controlling the wiper driving frequency.

Furthermore, as described in Embodiment 1, it is possible to change the content of the wiper control signal by presuming the type of the rainfall according to a rate of "low" signals detected among the photodetection signals of the photodetecting elements of the rain sensor 700. By monitoring the number of low signals detected per a unit time and presuming the type of rainfall according to the number of raindrops per a unit time, the wiper driving frequency is controlled.

The window wiper driving unit 720 receives a control signal transmitted from the window wiper controlling unit 710, and controls the driving of the window wiper 730.

The window wiper 730 is driven by a driving force given by the window wiper driving unit 720, and exhibits a suspended state and a driven state. As the driven state, a plurality of states may be exhibited, for instance, a state of being intermittently driven at a higher frequency, and a state of being intermittently driven at a lower frequency. In the driven state, a predetermined surface of the windshield is cleaned.

A flow of a processing operation of the window wiper controller will be described with reference to a flowchart of FIG. 12.

When the window wiper controller is operating (Operation Op101: Y), the window wiper controlling unit 710 receives photodetection signals from the photodetecting elements of the rain sensor 700, and monitors levels of the photodetection signals (Operation Op102). The window wiper controlling unit 710 checks whether any lower levels than a predetermined level or any "low" signals as digital values are included among the received photodetection signals (Operation Op103).

In the case where no lower levels than a predetermined level or no "low" signals as digital values are included among the received photodetection signals (Operation OP103: N), the window wiper controlling unit 710 determines that it does not rain or that it has stopped raining, and outputs a window wiper control signal for putting the window wiper 730 in a suspended state (Operation Op104). The window wiper driving unit 720 receives a control signal from the window wiper control unit 710, and maintains the window wiper 730 in a suspended state (Operation Op105). After the operation Op 105, the flow goes back to the operation Op 101 through a loop, and the control is continued (return to Operation Op110).

Assume that it starts raining, and raindrops adhere to the detection surface of the windshield. In the case where some lower levels than a predetermined level or some "low" signals as digital values are included among the received photodetection signals (Operation Op103: Y), the window wiper controlling unit 710 determines that it starts raining or it is raining (Operation Op106), and outputs a window wiper control signal for driving the window wiper 730, so as to clear the raindrops adhering to the windshield (Operation Op107). It should be noted that if it is possible to presume the type of the rainfall such as "drizzle", "light rain", and "heavy rain" as described as applied functions in addition to the detection of adhering raindrops, the presumed result may be used as a control signal for selecting the wiper driving frequency. The window wiper driving unit 720 receives a control signal from the window wiper control unit 710, and puts the window wiper 730 into a driven state (Operation Op108). After the operation Op108, the flow goes back to the operation Op101 through the loop so as to continue the control (return to Operation Op101).

With linkage and transfer of the foregoing flow of the processing operation without delay, the driving of the window wiper 730 is started immediately and surely when it starts raining, and it is stopped appropriately when it stops raining.

It should be noted that, to detect the size and the type of an object, the foregoing window wiper controller conducts the processing operation of digitalizing photodetection signals of the photodetecting elements 51 and analyzing the digital signals obtained, but for the same purpose, it may conduct a processing operation of generating a signal pattern of the photodetection signals of the photodetecting elements 51 according to the arrangement of the photodetecting elements 51 and analyzing a waveform of the signal pattern.

Figure 13:
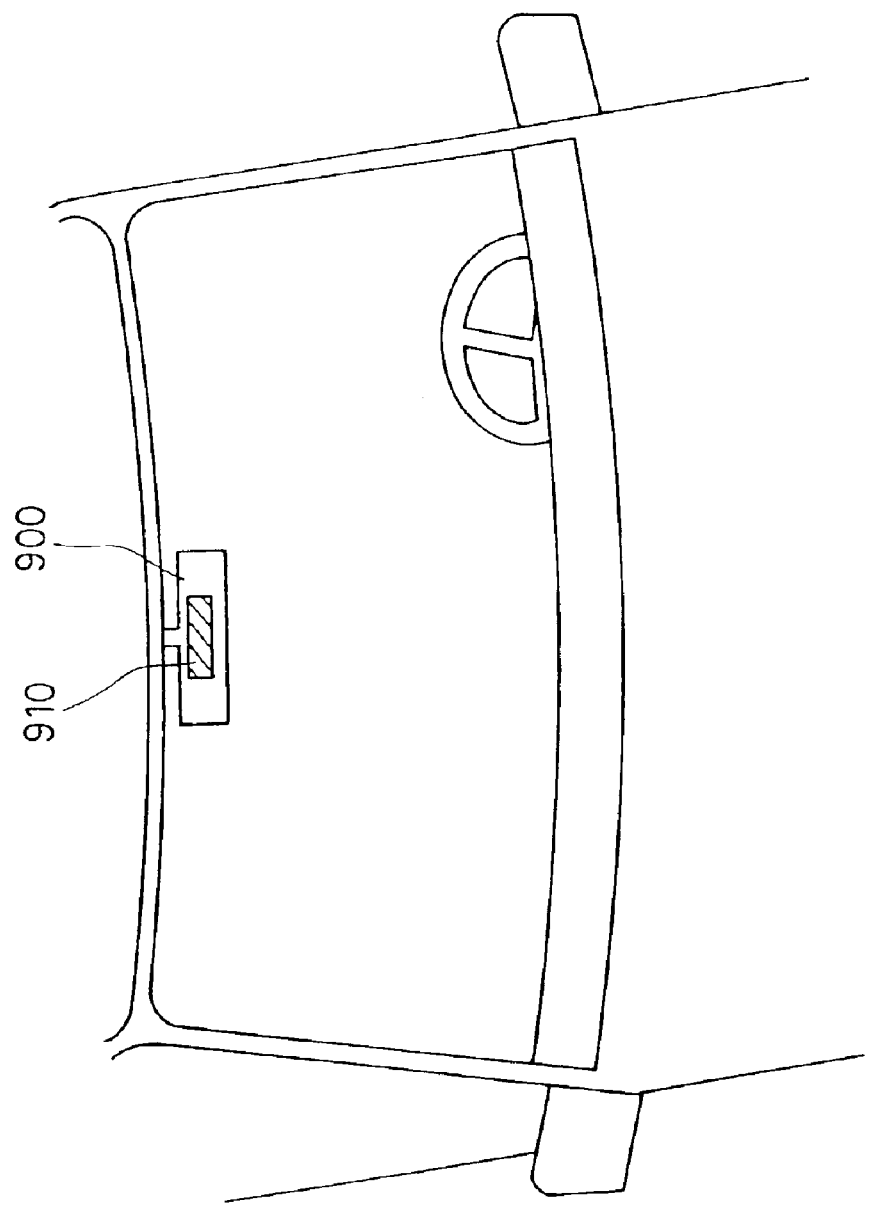
FIG. 13 is a view schematically illustrating an example of a manner of mounting of a window wiper controller employing the object sensor of the present invention as a rain sensor.
Figure 14:
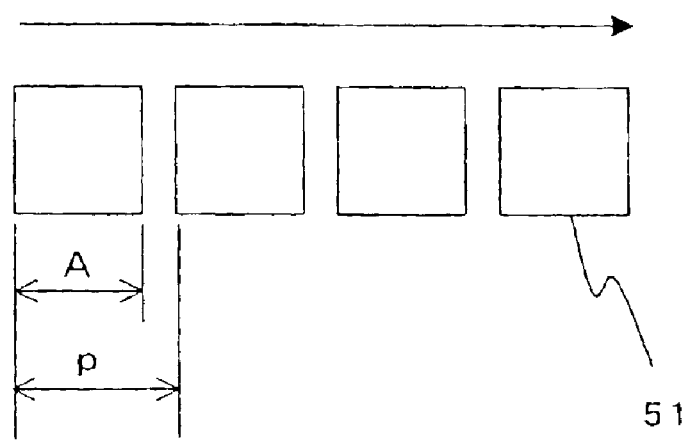
FIG. 14 is a view illustrating the relationship in which an arrangement pitch of the micro-photodetecting elements is set to be p, and a length of the micro-photodetecting element in the arrangement direction is set to be A.
Figure 17:
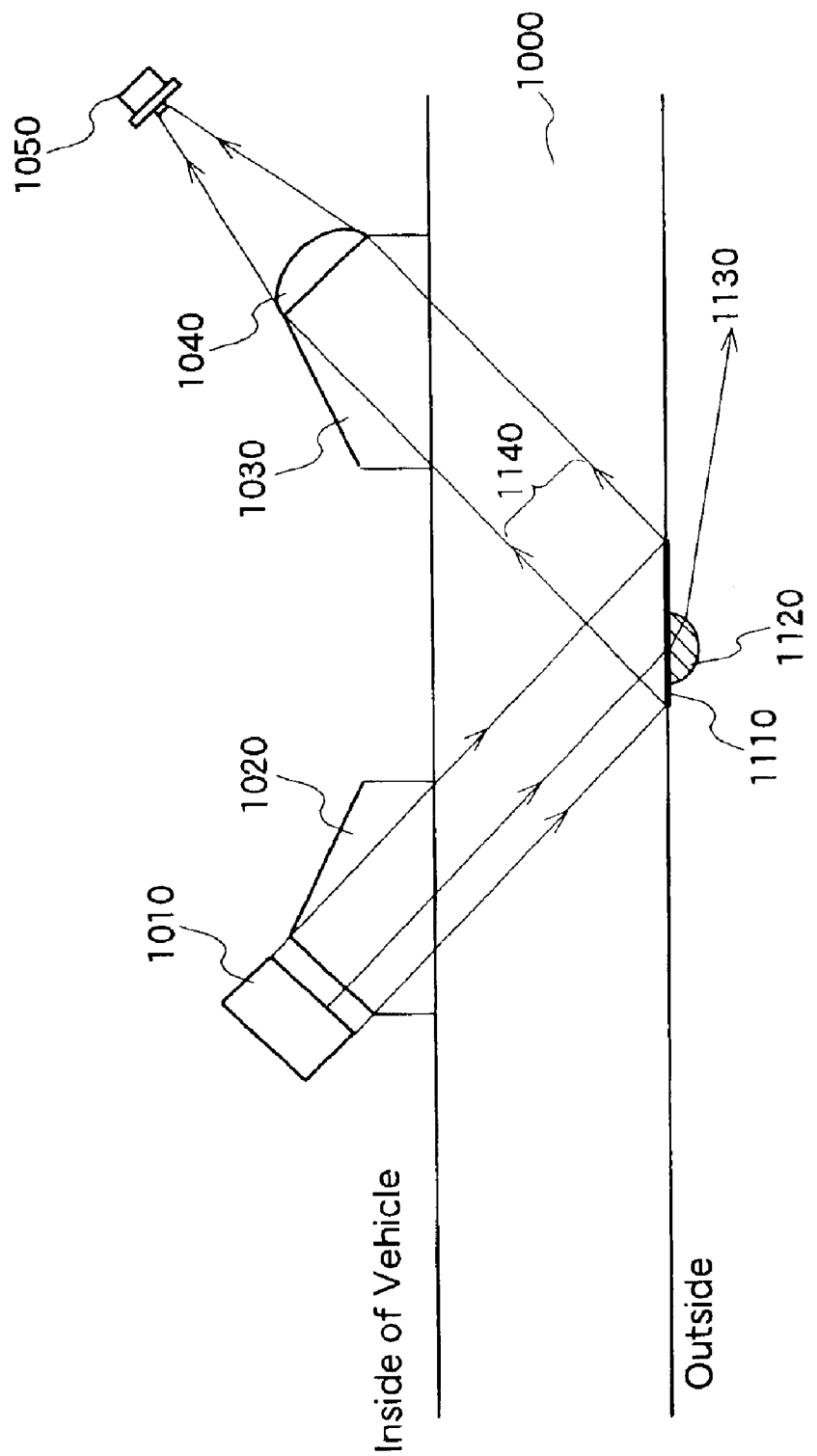
FIG. 17 is a view schematically illustrating a raindrop detecting principle of a conventional reflected-light-detecting-type rain sensor.

FIG. 13 is a view schematically illustrating an example of the provision of the window wiper controller employing the object sensor of the present invention as a rain sensor. As shown in FIG. 13, the rain sensor 700 as the object sensor is attached to a windshield portion 910 behind a rear-view mirror 900 of a vehicle. Thus, the arrangement of the sensor on the windshield portion 910 behind the rear-view mirror 900 makes it possible to secure the detection surface on the windshield without unnecessarily blocking the driver's vision for driving. The window wiper controlling unit 710 and the window wiper driving unit 720 are not shown in the drawing, but they are housed in a cabin as vehicle equipment in the vicinity of the window wiper 730.

In the foregoing description, the controller employing the object sensor described in Embodiment 3 is merely an example, and the object sensor of the present invention is not limited to the specific device configuration example described above. It may be configured in another manner based on the technological idea of the present invention, and may be used for purposes other than the window wiper controller.

INDUSTRIAL APPLICABILITY

According to the object sensor of the present invention, one micro-photodetecting element has a size smaller than a size of an image of an object to be detected, the image being formed on a photodetecting unit. Therefore, it is possible to determine the presence/absence of an object on the detection surface in detail, and hence, it is possible to determine the presence/absence of a small object with a high sensitivity.

Furthermore, according to the object sensor of the present invention, an object is sensed by a plurality of micro-photodetecting elements. This allows for an increase in an area of the detection surface to be sensed by these micro-photodetecting elements, which raises the object detection probability.

Furthermore, according to the object sensor of the present invention, a change in the photodetection signal of the micro-photodetecting element is significant due to the presence/absence of an object on a corresponding portion of the detection surface. Therefore, it is possible to determine the presence/absence of an object with a high sensitivity, and to treat the photodetection signal as a digital signal obtained by binarization.

Furthermore, according to the object sensor of the present invention, a signal pattern is obtained by detecting reflected light from the detection surface using a plurality of micro-photodetecting elements and arranging photodetection signals obtained from the photodetecting elements according to the arrangement of the micro-photodetecting elements. Therefore, it is possible to determine the presence/absence of a raindrop or the like adhering to the detection surface with a high sensitivity by analyzing relative variances in micro domains of the signal pattern, that is, variation in a waveform.

Furthermore, according to the object sensor of the present invention, by checking which micro-photodetecting element among the arranged micro-photodetecting elements provides a great change in a photodetection signal, an approximate size and shape of an object can be presumed based on the arrangement of the micro-photodetecting elements corresponding to a portion of the detection surface covered by the object.

What is claimed is:

1. An object sensor comprising:
   a light-emitting unit for emitting light to a transparent substrate, the transparent substrate having a detection surface on which the light emitted from the light-emitting unit and introduced into the transparent substrate is reflected;
   a photodetecting unit for receiving the light reflected on the detection surface; and
   an object sensing unit for sensing presence of an object on the detection surface by detecting a change in a photodetection signal obtained as a result of photodetection of the photodetecting unit, the change being caused by a change in a reflection condition on the detection surface which is caused by the object,
   wherein the light-emitting unit and the photodetecting unit are arranged with respect to the transparent substrate so that the reflected light is received by the photodetecting unit, and so that a photodetecting surface of the photodetecting unit and the detection surface form a focusing optical system,
   the light-emitting unit is a linear or planar light source formed by providing a plurality of light sources at either one or both of ends of a photoconductor,
   the focusing optical system is a focusing system of equal magnification, and
   the photodetecting unit includes a plurality of micro-photodetecting elements.

2. The object sensor according to claim 1, wherein each micro-photodetecting element has a size smaller than a size of an image of the object to be sensed that is formed on the photodetecting unit.

3. The object sensor according to claim 2, wherein each micro-photodetecting element has an effective area of not greater than 0.2 mm$^2$.

4. The object sensor according to claim 2, wherein each micro-photodetecting element has an effective area of not greater than 0.03 mm$^2$.

5. The object sensor according to claim 2, wherein the plurality of micro-photodetecting elements of the photodetecting unit are arranged in a linear form, or in a two-dimensional form.

6. The object sensor according to claim 1, wherein a sum of a length A of each micro-photodetecting element in a direction in which the micro-photodetecting elements are arranged and a pitch p at which the micro-photodetecting elements are arranged is smaller than a dimension D of an image of the object to be sensed, the image being formed on the photodetecting unit.

7. The object sensor according to claim 6, wherein a group composed of micro-photodetecting elements at every n positions in the arrangement of the micro-photodetecting elements is selected as micro-photodetecting elements that are to operate among the plurality of micro-photodetecting elements, with n being a natural number.

8. The object sensor according to claim 5, wherein a shape of the object on the detection surface is presumed based on the arrangement of the plurality of micro-photodetecting elements and variances in a signal pattern obtained from the photodetection signals of the arranged micro-photodetecting elements.

9. The object sensor according to claim 1, wherein arrangement angles of the light-emitting unit, the transparent substrate, the focusing optical system, and the photodetecting unit are selected according to a refractive index of a material present between outside and the photodetecting unit so as to prevent external light entering the transparent substrate through its outside surface from directly entering the photodetecting unit.

10. The object sensor according to claim 9, wherein the arrangement angles of the light-emitting unit, the transparent substrate, the focusing optical system, and the photodetecting unit are selected so as to satisfy the following formula:

$$\sin^{-1}\left(\frac{n_1}{n_3}\right) + \left(\frac{\theta_S}{n_3}\right) < \theta_5$$

where $n_1$ represents a refractive index of a medium on an outside surface side of the transparent substrate, $n_3$ represents a refractive index of a medium present between the transparent substrate and the focusing optical system, $\theta_5$ represents a mounting angle of the focusing optical system, and $\theta_S$ represents an angular aperture of the focusing optical system.

11. The object sensor according to claim 1, wherein
   the light-emitting unit, the transparent substrate, the focusing optical system, and the photodetecting unit are arranged so that light emitted from the light-emitting unit and reflected on the detection surface enters the photodetecting unit in the case where the object is absent on the detection surface, and arrangement angles of the light-emitting unit, the transparent substrate, the focusing optical system, and the photodetecting unit are selected so that, in the case where the object is present on the detection surface, a change in the reflection condition on the detection surface caused by the object causes light emitted from the light-emitting unit not to be reflected on the detection surface.

12. The object sensor according to claim 11, wherein the arrangement angles of the light-emitting unit, the transparent substrate, the focusing optical system, and the photodetecting unit are selected so as to satisfy the following formula:

$$\sin^{-1}\left(\frac{n_1}{n_3}\right) < \theta_2 < \sin^{-1}\left(\frac{n_1'}{n_3}\right)$$

where $n_1$ represents a refractive index of a medium on an outside surface side of the transparent substrate, $n_3$ represents a refractive index of a medium present between the transparent substrate and the focusing optical system, $n_1'$ represents a refractive index of the object, and $\theta_2$ represents an angle of refraction at which the light is refracted upon entry to the transparent substrate.

13. The object sensor according to claim 1, wherein the light-emitting unit, the transparent substrate, the focusing optical system, and the photodetecting unit are arranged so that light emitted from the light-emitting unit and reflected on the detection surface enters the photodetecting unit in the case where the object is absent on the detection surface, arrangement angles of the light-emitting unit, the transparent substrate, the focusing optical system, and the photodetecting unit are selected so that, in the case where the object is present on the detection surface, a change in the reflection condition caused on the detection surface by the object causes light emitted from the light-emitting unit not to be reflected on the detection surface, and the arrangement angles of the light-emitting unit, the transparent substrate, the focusing optical system, and the photodetecting unit are selected also according to a refractive index of a material present between outside and the photodetecting unit so as to prevent external light entering the transparent substrate through its outside surface from directly entering the photodetecting unit.

14. The object sensor according to claim 13, wherein the arrangement angles of the light-emitting unit, the transparent substrate, the focusing optical system, and the photodetecting unit are selected so as to satisfy the following formulae (A) and (B):

$$\sin^{-1}\left(\frac{n_1}{n_3}\right) + \left(\frac{\theta_s}{n_3}\right) < \theta_S \tag{A}$$

$$\sin^{-1}\left(\frac{n_1}{n_3}\right) < \theta_2 < \sin^{-1}\left(\frac{n_1'}{n_3}\right) \tag{B}$$

where $n_1$ represents a medium on an outside surface of the transparent substrate, $n_3$ represents a medium present between the transparent substrate and the focusing optical system, $n_1'$ represents a refractive index of the object, $\theta_2$ represents an angle of refraction at which the light is refracted upon entry to the transparent substrate, $\theta_5$ represents a mounting angle of the focusing optical system, and $\theta_S$ represents an angular aperture of the focusing optical system.

15. The object sensor according to claim 9, wherein in the selection of the arrangement angles of the light-emitting unit, the transparent substrate, the focusing optical system, and the photodetecting unit, the arrangement angles are selected so that a path inside the transparent substrate along which the light emitted by the light-emitting unit and reflected on the detection surface travels is minimized in length.

16. The object sensor according to claim 1, wherein the object to be sensed is a raindrop and the detection surface is provided on a windshield of a vehicle so that the object sensor is used as a rain sensor for detecting presence of a raindrop adhering to the windshield.

17. A window wiper device comprising:

the object sensor according to claim 16;

a window wiper driving unit; and a window wiper controlling unit, wherein the window wiper controlling unit receives a detection signal concerning an object from the object sensor, and changes control status of the window wiper driving unit according to the detection signal.

* * * * *